United States Patent
Wolff et al.

(10) Patent No.: US 7,144,869 B2
(45) Date of Patent: *Dec. 5, 2006

(54) NUCLEIC ACID INJECTED INTO HAPATIC VEIN LUMEN AND DELIVERED TO PRIMATE LIVER

(75) Inventors: Jon A. Wolff, Madison, WI (US); Julia Hegge, Monona, WI (US); James E. Hagstrom, Middleton, WI (US); Vladimir G. Budker, Middleton, WI (US)

(73) Assignee: Mirus Bio Corporation, Madison, WI (US)

( * ) Notice: Subject to any disclaimer, the term of this patent is extended or adjusted under 35 U.S.C. 154(b) by 569 days.

This patent is subject to a terminal disclaimer.

(21) Appl. No.: 10/310,398

(22) Filed: Dec. 5, 2002

(65) Prior Publication Data

Related U.S. Application Data

(60) Continuation-in-part of application No. 09/477,966, filed on Nov. 23, 1999, now Pat. No. 6,627,616, which is a continuation-in-part of application No. 09/391,260, filed on Sep. 7, 1999, now abandoned, which is a division of application No. 08/975,483, filed on Nov. 21, 1997, now Pat. No. 6,265,387, which is a continuation of application No. 08/571,536, filed on Dec. 13, 1995, now abandoned.

(51) Int. Cl.
*A61K 31/70* (2006.01)
*C12N 15/74* (2006.01)

(52) U.S. Cl. ............ 514/44; 435/320.1; 435/455; 536/23.1; 536/24.5

(58) Field of Classification Search .............. None
See application file for complete search history.

(56) References Cited

U.S. PATENT DOCUMENTS 6,265,387 B1 * 7/2001 Wolff et al. .................. 514/44
6,627,616 B1 * 9/2003 Monahan et al. ............ 514/44

OTHER PUBLICATIONS

Zhang et al, Hum Gene Ther 1999,10:1735-7.*
Zhang et al, Hum Gene Ther 1997;8:1763-72.*
Robaczewska et al, Gene Ther Jun. 2001;8:874-81.*
Park et al, Nucleic Acids Res 2001;S1:219-20.*
Acsadi G et al. "Direct gene transfer and expression into rat heart in vivo," The New Biologist; 1991 vol. 3, No. 1 pp. 71-81.
Alford FP et al. "The secretion rate of human growth hormone. I. Daily secretion rates, effect of posture and sleep," J Clin Endocrinol Metab; 1973 vol. 37, No. 4 pp. 515-520.
Andree C et al. "In vivo transfer and expression of a human epidermal growth factor gene accelerates wound repair," Proc. Natl Acad Sci USA; 1994 vol. 91, No. 25 pp. 12188-12192.
Browning J et al. "Capillary density in skeletal muscle of Wistar rats as a function of muscle weight and body weight," Microvasc Res; 1996 vol. 52, No. 3 pp. 281-287.
Budker V et al. "Naked DNA delivered intraportally expresses efficiently in hepatocytes," Gene Ther; 1996 vol. 3, No. 7 pp. 593-598.
Chapman GD et al. "Gene transfer into coronary arteries of intact animals with a percutaneous ballon catheter," Circ Res; 1992 vol. 71, No. 1 pp. 27-33.
Chowdhury JR et al. "Long-term improvement of hypercholesterolemia after ex vivo gene therapy in LDLR-deficient rabbits," Science; 1991 vol. 254, No. 5039 pp. 1802-1805.
Danko I et al. "Pharmacological enhancement of in vivo foreign gene expression in muscle," Gene Ther; 1994 vol. 1, No. 2 pp. 114-121.
Desmet VJ et al. "Tight junctions in the liver," Prog Liver Dis; 1982 vol. 7 pp. 31-50.
Evans WS et al. "Impact of intensive venous sampling on characterization of pulsatile GH release," Am J Physiol; 1987 vol. 252, No. 4 Pt. 1 pp. E549-E556.
Faria AC et al. "Half-time of endogenous growth hormone (GH) disappearance in normal man after stimulation of GH secretion by GH-releasing hormone and suppression with somatostain," J Clin Endocrinol Metab; 1989 vol. 68, No. 3 pp. 535-541.
Ferry N et al. "Retroviral-mediated gene transfer into hepatocytes in vivo," Proc Natl Acad Sci U S A; 1991 vol. 88, No. 19 pp. 8377-8381.
Fishman DM et al. "Light scattering studies of supercoiled and nicked DNA," Biopolymers; 1996; vol. 38 No. 4 pp. 535-552.
Gidlof A et al. "The effect of prolonged total ischemia on the ultrastructure of human skeletal muscle capillaries. A morphometric analysis," Int J Microcirc Clin Exp; 1988 vol. 7, No. 1 pp. 67-86.
Grossman M et al. "Successful ex vivo gene therapy directed to liver in a patient with familial hypercholesterolaemia," Nat Genet; 1994 vol. 6, No. 4 pp. 335-341.
Haussinger D. "The role of cellular hydration in the regulation of cell function," Biochem J; 1996 vol. 313, No. 3 pp. 697-710.
Haussinger D et al. "Cell volume and bile acid excretion," Biochem J; 1992 vol. 288, No. 2 pp. 681-689.
Hengge UR et al. "Cytokine gene expression in epidermis with biological effects following injection of naked DNA," Nat Genet; 1995; vol. 10, No. 2 pp. 161-166.
Herweijer H et al. "A plasmid-based self-amplifying Sindbis virus vector," Hum Gene Ther; 1995; vol. 6, No. 9 pp. 1161-1167.
Hickman MA et al. "Gene expression following direct injection of DNA into liver," Hum Gene Ther; 1994 vol. 5, No. 12 pp. 1477-1483.

(Continued)

*Primary Examiner*—Q. Janice Li
(74) *Attorney, Agent, or Firm*—Mark K. Johnson; Kirk Evans

(57) ABSTRACT

Processes are described for obtaining high levels of gene expression in primates after injection of nucleic acid to the liver via the lumen of the hepatic vein. The described process results in high level of gene expression with transient increases in liver enzymes.

15 Claims, No Drawings

OTHER PUBLICATIONS

Holl RW et al. "Thirty-second sampling of plasma growth hormone in man: correlation with sleep stages," J Clin Endocrinol Metab; 1991 vol. 72, No. 4 pp. 854-861.

Jaffe HA et al. "Adenovirus-mediated in vivo gene transfer and expression in normal rat liver," Nat Genet; 1992 vol. 1, No. 5 pp. 372-378.

Jiao S et al. "Direct gene transfer into nonhuman primate myofibers in vivo," Hum Gene Ther; 1992 vol. 3, No. 1 pp. 21-33.

Kaleko M et al. "Persistent gene expression after retroviral gene transfer into liver cells in vivo," Hum Gene Ther; 1991 vol. 2, No. 1 pp. 27-32.

Kaneda Y et al. "Increased expression of DNA cointroduced with nuclear protein in adult rat liver," Science; 1989 vol. 243, No. 4889 pp. 375-378.

Kaneda Y et al. "Introduction and expression of the human insulin gene in adult rat liver," J Biol Chem; 1989 vol. 264, No. 21 pp. 12126-12129.

Kay MA et al. "Hepatic gene therapy: persistent expression of human alpha 1-antitrypsin in mice after direct gene delivery in vivo," Hum Gene Ther; 1992 vol. 3, No. 6 pp. 641-647.

Ledley FD et al. "Retroviral gene transfer into primary hepatocytes: implications for genetic therapy of liver-specific functions," Proc. Natl Acad Sci U S A; 1987 vol. 84, No. 15 pp. 5335-5339.

Lee J et al. "Biomechanics of skeletal muscle capillaries: hemodynamic resistance endothelial distensibility, and pseudopod formation," Ann Biomed Eng; 1995 vol. 23, No. 3 pp. 226-246.

Li Q et al. "Assessment of recombinant adenoviral vectors for hepatic gene therapy," Hum Gene Ther; 1993 vol. 4, No. 4 pp. 403-409.

Malone RW et al. "Dexamethasone enhancement of gene expression after direct hepatic DNA injection," J Biol Chem; 1994 vol. 269, No. 47 pp. 29903-29907.

Mathieu-Costello O et al. "Capillary ultrastructure and functional capillary density," Int J Microcirc Clin Exp; 1995 vol. 15, No. 5 pp. 231-237.

Meyer KB et al. "Intratracheal gene delivery to the mouse airway: characterization of plasmid DNA expression and pharmacokinetics," Gene Ther; 1995 vol. 2, No. 7 pp. 450-460.

Michel CC. "Transport macromolecules through microvascular walls," Cardiovasc Res; 1996 vol. 32, No. 4 pp. 644-653.

Nabel EG et al. "Gene transfer in vivo with DNA-liposome complexes: lack of autoimmunity and gonadal localization," Hum Gene Ther; 1992 vol. 3, No. 6 pp. 649-656.

Offensperger WB et al. "Effects of anisotonic exposure on duck hepatitis B virus replication," Hepatology; 1994 vol. 20, No. 1 Pt. 1 pp. 1-7.

Peeters S et al. "A growth hormone binding factor in the serum of pregnant mice," Endocrinology; 1977 vol. 101, No. 4 pp. 1164-1183.

Peeters MJ et al. "Adenovirus-mediated hepatic gene transfer in mice: comparison of intravascular and biliary administration," Hum Gene Ther; 1996 vol. 7, No. 14 pp. 1693-1699.

Picard D et al. "Two signals mediate hormone-dependent nuclear localization of the glucocorticoid receptor," EMBO J; 1987 vol. 6, No. 11 pp. 3333-3340.

Riessen R et al. "Arterial gene transfer using pure DNA applied directly to a hydrogel-coated angioplasty balloon," Hum Gene Ther; 1993 vol. 4, No. 6 pp. 749-758.

Rippe B et al. "Evaluation of the 'stretched pore phenomenon' in isolated rat hindquarters," Acta Physiol Scand; 1985 vol. 125, No. 3 pp. 453-459.

Rippe B et al. "Transport of macromolecules across microvascular walls: the two-pore theory," Physiol Rev; 1994 vol. 74, No. 1 pp. 163-219.

Rybenkov et al. "The effect of ionic conditions on the conformations of supercoiled DNA. I. Sedimentation analysis," J Mol Biol; 1997 vol. 267, No. 2 pp. 299-311.

Sikes ML et al. "In vivo gene transfer into rabbit thyroid follicular cells by direct DNA injection," Hum Gene Ther; 1994 vol. 5, No. 7 pp. 837-844.

Soriano P et al. "Targeted and nontargeted liposomes for in vivo transfer to rat liver cells of a plasmid containing the preproinsulin I gene," Proc Natl Acad Sci U S A; 1983 vol. 80, No. 23 pp. 7128-7131.

Stieger B et al. "Effect of obstructive cholestasis on membrane traffic and domain-specific expression of plasma membrane proteins in rat liver parenchymal cells," Hepatology, 1994 vol. 20, No. 1 Pt. 1 pp. 201-212.

Stratford-Perricaudet LD et al. "Evaluation of the transfer and expression in mice of an enzyme-encoding gene using a human adenovirus vector," Hum Gene Ther; 1990 vol. 1, No. 3 pp. 241-256.

Taylor AE et al. "Exchange of macromolecules across the microcirculation," In: Handbook of Physiolog The Cardiovascular System Microcirculation. Bethesda, MD: A Physio So, 1984, sec 2 vol. IV, chap 11, 467.

Vile RG et al. "Use of tissue-specific expression of the herpes simplex virus thymidine kinase gene to inhibit growth of established murine melanomas following direct intratumoral injection of DNA," Cancer Res; 1993 vol. 53, No. 17 pp. 3860-3864.

Vrancken-Peeters MJ et al. "Method for multiple portal vein infusions in mice: quantitation of adenovirus-mediated hepatic gene transfer," Biotechniques; 1996 vol. 20, No. 2 pp. 278-285.

Webber EM et al. "Overexpression of transforming growth factor-alpha causes liver enlargement and increased hepatocyte proliferation in transgenic mice," Am J Pathol; 1994 vol. 145, No. 2 pp. 398-408.

Wolf MB et al. "Effects of elevated venous pressure capillary permeability in cat hindlimbs," Am J Physiol; 1989 vol. 257, No. 6 Pt. 2 pp. H2025-H2032.

Wolff JA et al. "Expression of retrovirally transduced genes in primary cultures of adult rat hepatocytes," Proc Natl Acad Sci U S A; 1987 vol. 84, No. 10 pp. 3344-3348.

Wolff JA et al. "Direct gene transfer into mouse muscle in vivo," Science; 1990 vol. 247 pp. 1465-1466.

Wolff JA et al. "Conditions affecting direct gene transfer into rodent muscle in vivo," Biotechniques; 1991 vol. 11, No. 4 pp. 474-485.

Wolff JA et al. "Expression of naked plasmids by cultured myotubes and entry of plasmids into T tubules and caveolae of mammalian skeletal muscle," J Cell Sci; 1992 vol. 103, No. 4 pp. 1249-1259.

Wolff JA et al. "Long-term persistence of plasmid DNA and foreign gene expression in mouse muscle," Hum Mol Genet; 1992 vol. 1, No. 6 pp. 363-369.

Wu GY et al. "Receptor-mediated gene delivery and expression in vivo," J Biol Chem; 1988 vol. 263, No. 29 pp. 14621-14624.

Yang Y et al. "Immune responses to viral antigens versus transgene product in the elimination of recombinant adenovirus-infected hepatocytes in vivo," Gene Ther; 1996 vol. 3, No. 2 pp. 137-144.

Yang D et al. "Coordinate expression of N-myc 2 and insulin-like growth factor II in precancerous altered hepatic foci in woodchuck hepatitis virus carries," Cancer Res; 1993 vol. 53, No. 9 pp. 2020-2027.

Roos DE et al. "Isolated organ perfusion for local gene delivery: efficient adenovirus mediated gene transfer into the liver." Gene Therapy, 1997 vol. 4, No. 1, p. 55-62.

Nones FA et al. "Gene Transfer into the liver of nonhuman primates with E1-delted recombinant adenoviral vectors: safety of readminstration." Human Gene Therapy 1999 vol. 10, No. 15, p. 2515-5256.

Raper SE et al. "Selective gene transfer into the liver of non-human primates with E1-deleted, E2A-defective, or E1-E4 deleted recombinant adenoviruses." Human Gene Therapy 1998 vol. 9, p. 671-679.

* cited by examiner

NUCLEIC ACID INJECTED INTO HAPATIC VEIN LUMEN AND DELIVERED TO PRIMATE LIVER

CROSS-REFERENCE TO RELATED APPLICATIONS

This Application is a continuation-in-part of U.S. application Ser. No. 09/447,966, filed Nov. 23, 1999, now U.S. Pat. No. 6,627,616, which is a continuation-in-part of application Ser. No. 09/391,260, filed Sep. 7, 1999, abandoned, which is a divisional of application Ser. No. 08/975,573, filed Nov. 21, 1997 now U.S. Pat. No. 6,265,387, which is a continuation of application Ser. No. 08/571,536, filed Dec. 13, 1995, abandoned.

FIELD OF THE INVENTION

The invention generally relates to techniques for transferring genes into mammalian parenchymal cells in vivo. More particularly, a method is provided for transfecting hepatic cells with polynucleotides delivered intravascularly under pressure.

BACKGROUND OF THE INVENTION

It was first observed that the in vivo injection of plasmid DNA into muscle enabled the expression of foreign genes in the muscle (Wolff, J A, Malone, R W, Williams, P, et al. Direct gene transfer into mouse muscle in vivo. *Science* 1990;247: 1465–1468.). Since that report, several other studies have reported the ability for foreign gene expression following the direct injection of DNA into the parenchyma of other tissues. Naked DNA was expressed following its injection into cardiac muscle (Acsadi, G., Jiao, S., Jani, A., Duke, D., Williams, P., Chong, W., Wolff, J. A. Direct gene transfer and expression into rat heart in vivo. The New Biologist 3(1), 71–81, 1991.), pig epidermis (Hengge, U. R., Chan, E. F., Foster, R. A., Walker, P. S., and Vogel, J. C. Nature Genetics 10:161–166 (1995)), rabbit thyroid (M. Sikes, B. O'Malley, M. Finegold, and F. Ledley, Hum. Gene Ther. 5, 837 (1994), lung by intratracheal injection (K. B. Meyer, M. M. Thompson, M. Y. Levy, L. G. Barron, F. C. Szoka, Gene Ther. 2, 450 (1995)), into arteries using a hydrogel-coated angioplasty balloon (R. Riessen et al, Human Gene Ther. 4, 749 (1993)) (G. Chapman et al. Circ. Res. 71, 27 (1992)), melanoma tumors (R. G. Vile and I. R. Hart, Cancer Res. 53, 962 (1993)) and rat liver [(Malone, R. W. et al. JBC 269:29903–29907 (1994)) (Hickman, M. A. Human Gene Therapy 5:1477–1483 (1994))].

Another important target tissue for gene therapy is the mammalian liver, given its central role in metabolism and the production of serum proteins. A variety of techniques have been developed to transfer genes into the liver. Cultured hepatocytes have been genetically modified by retroviral vectors [(Wolff, J. A. et al. PNAS 84:3344–3348 (1987) (Ledley, F. D., Darlington, G. J., Hahn, T. and Woo, S.C.L. PNAS 84:5335–5339 (1987)] and re-implanted back into the livers in animals and in people [(J. R. Chowdhury et al. Science 254, 1802 (1991) (M. Grossman et al. Nature Genetics 6, 335 (1994)]. Retroviral vectors have also been delivered directly to livers in which hepatocyte division was induced by partial hepatectomy [(Kay, M. A. et al Hum Gene Ther. 3:641–647 (1992) (Ferry, N., Duplessis, O., Houssin, D., Danos, O. and Heard, J.-M. PNAS 88:8377–8381 (1991) (Kaleko, M., Garcia, J. V. and Miller, A. D. Hum Gene THer. 2:27–32 (1991)]. The injection of adenoviral vectors into the portal or systemic circulatory systems leads to high levels of foreign gene expression that is transient [(L. D. Stratford-Perricaudet, M. Levrero, J. F. Chasse, M. Perricaudet, P. Briand, Hum. Gene Ther. 1, 241 (1990) (H. A. Jaffe et al. Nat. Genet. 1, 372 (1992) (Q. Li, M. A. Kay, M. Finegold, L. D. Stratford-Perricaudet, S. L. C. Woo, Hum. Gene Ther. 4, 403 (1993)]. Non-viral transfer methods have included polylysine complexes of asialoglycoproteins that are injected into the system circulation [Wu, G. Y. and Wu, C. H. J. Biol. Chem. 263:14621–14624 (1988)].

Foreign gene expression has also been achieved by repetitively injecting naked DNA in isotonic solutions into the liver parenchyma of animals treated with dexamethasone [(Malone, R. W. et al. JBC 269:29903–29907 (1994) (Hickman, M. A. Human Gene Therapy 5:1477–1483 (1994)]. Plasmid DNA expression in the liver has also been achieved via liposomes delivered by tail vein or intraportal routes [(Kaneda, Y., Kunimitsu, I. and Uchida, T. J. Biol. Chem. 264:12126–12129 (1989) (Soriano, P. et al. PNAS 80:7128–7131 (1983) Kaneda, Y., Iwai, K. and Uchida, T. Science 243:375–378 (1989)].

Despite this progress, there is still a need for a gene transfer method that can efficiently and safely cause the expression of foreign genes in the liver in a and/or repetitive manner.

SUMMARY OF THE INVENTION

The present invention provides for the transfer of polynucleotides into parenchymal cells within tissues in situ and in vivo. An intravascular route of administration enables a prepared polynucleotide to be delivered to the parenchymal cells more evenly distributed and more efficiently expressed than direct parenchymal injections. The efficiency of polynucleotide delivery and expression was increased substantially by increasing the permeability of the tissue's blood vessel. This was done by increasing the intravascular hydrostatic (physical) pressure and/or increasing the osmotic pressure. Expression of a foreign DNA was obtained in mammalian liver by intraportally injecting plasmid DNA in a hypertonic solution and transiently clamping the hepatic vein/inferior vena cava. Optimal expression was obtained by clamping the portal vein and injecting the hepatic vein/inferior vena cava.

A process is described for delivering a polypeptide into a parenchymal cell in a mammal, comprising, transporting the polynucleotide into a vessel communicating with the parenchymal cell of the mammal such that the polynucleotide is transfected into the parenchymal cell.

A process for delivering a coded polynucleotide into a parenchymal cell of a mammal for expression of a protein, comprising, transporting the polynucleotide to a vessel containing a fluid and having a permeable wall; and, increasing the permeability of the wall for a time sufficient to complete delivery of the polynucleotide.

DETAILED DESCRIPTION

A. Definitions

The term, naked polynucleotides, indicates that the polynucleotides are not associated with a transfection reagent or other delivery vehicle that is required for the polynucleotide to be delivered to the parenchymal cell. A transfection reagent is a compound or compounds used in the prior art that bind(s) to or complex(es) with polynucleotides and mediates their entry into cells. The transfection reagent also mediates the binding and internalization of polynucleotides into cells. Examples of transfection reagents include cationic liposomes and lipids, calcium phosphate precipitates, and polylysine complexes. Typically, the transfection reagent has a net positive charge that binds to the polynucleotide's negative charge. The transfection reagent mediates binding of polynucleotides to cell via its positive charge (that binds to the cell membrane's negative charge) or via ligands that bind to receptors in the cell. For example, cationic liposomes or polylysine complexes have net positive charges that enable them to bind to DNA. Other vehicles are also used, in the prior art, to transfer genes into cells. These include complexing the polynucleotides on particles that are then accelerated into the cell. This is termed biolistic or gun techniques. Other methods include eletroporation in which a device is used to give an electric charge to cells. The charge increases the permeability of the cell.

The term polynucleotide is a term of art that refers to a string of at least two base-sugar-phosphate combinations. Nucleotides are the monomeric units of nucleic acid polymers. The term includes deoxyribonucleic acid (DNA) and ribonucleic acid (RNA) in the form of an oligonucleotide messenger RNA, anti-sense, plasmid DNA, parts of a plasmid DNA or genetic material derived from a virus. A polynucleotide is distinguished, here, from a oligonucleotide by containing more than 120 monomeric units. Anti-sense is a polynucleotide that interferes with the function of DNA and/or RNA. A polynucleotide is considered in this specification to include a non-natural polynucleotide (not occurring in nature), for example: a derivative of natural nucleotides such as phosphothionates or peptide nucleic acids.

A polynucleotide can be delivered to a cell in order to produce a cellular change that is therapeutic. The delivery of polynucleotides or other genetic material for therapeutic purposes (the art of improving health in an animal including treatment or prevention of disease) is gene therapy. The polynucleotides are coded to express a whole or partial protein, or may be anti-sense, and can be delivered either directly to the organism in situ or indirectly by transfer to a cell that is then transplanted into the organism. The protein can be missing or defective in an organism as a result of genetic, inherited or acquired defect in its genome.

For example, a polynucleotide may be coded to express the protein dystrophin that is missing or defective in Duchenne muscular dystrophy. The coded polynucleotide is delivered to a selected group or groups of cells and incorporated into those cell's genome or remain apart from the cell's genome. Subsequently, dystrophin is produced by the formerly deficient cells. Other examples of imperfect protein production that can be treated with gene therapy include the addition of the protein clotting factors that are missing in the hemophilias and enzymes that are defective in inborn errors of metabolism such as phenylalanine hydroxylase.

A delivered polynucleotide can also be therapeutic in acquired disorders such as neurodegenerative disorders, cancer, heart disease, and infections. The polynucleotide has its therapeutic effect by entering the cell. Entry into the cell is required for the polynucleotide to produce the therapeutic protein, to block the production of a protein, or to decrease the amount of a RNA.

Additionally, a polynucleotide can be delivered to block gene expression. Such polynucleotides can be anti-sense by preventing translation of a messenger RNA or could block gene expression by preventing transcription of the gene. Small inhibiting RNA (siRNA) can also be used to inhibit gene expression. Preventing both RNA translation as well as DNA transcription is considered preventing expression. Transcription can be blocked by the polynucleotide binding to the gene as a duplex or triplex. It could also block expression by binding to proteins that are involved in a particular cellular biochemical process.

Polynucleotides may be delivered that recombine with genes. The polynucleotides may be DNA, RNA, hybrids and derivatives of natural nucleotides. Recombine is the mixing of the sequence of a delivered polynucleotide and the genetic code of a gene. Recombine includes changing the sequence of a gene.

Delivery of a polynucleotide means to transfer a polynucleotide from a container outside a mammal to within the outer cell membrane of a cell in the mammal. The term transfection is used herein, in general, as a substitute for the term delivery, or, more specifically, the transfer of a polynucleotide from directly outside a cell membrane to within the cell membrane. If the polynucleotide is a primary RNA transcript that is processed into messenger RNA, a ribosome translates the messenger RNA to produce a protein within the cytoplasm. If the polynucleotide is a DNA, it enters the nucleus where it is transcribed into a messenger RNA that is transported into the cytoplasm where it is translated into a protein. The polynucleotide contains sequences that are required for its transcription and translation. These include promoter and enhancer sequences that are required for initiation. DNA and thus the corresponding messenger RNA (transcribed from the DNA) contains introns that must be spliced, poly A addition sequences, and sequences required for the initiation and termination of its translation into protein. Therefore if a polynucleotide expresses its cognate protein, then it must have entered a cell.

A therapeutic effect of the protein in attenuating or preventing the disease state can be accomplished by the protein either staying within the cell, remaining attached to the cell in the membrane or being secreted and dissociating from the cell where it can enter the general circulation and blood. Secreted proteins that can be therapeutic include hormones, cytokines, growth factors, clotting factors, antiprotease proteins (e.g. alpha-antitrypsin) and other proteins that are present in the blood. Proteins on the membrane can have a therapeutic effect by providing a receptor for the cell to take up a protein or lipoprotein. For example, the low density lipoprotein (LDL) receptor could be expressed in hepatocytes and lower blood cholesterol levels and thereby prevent atherosclerotic lesions that can cause strokes or myocardial infarction. Therapeutic proteins that stay within the cell can be enzymes that clear a circulating toxic metabolite as in phenylketonuria. They can also cause a cancer cell to be less proliferative or cancerous (e.g. less metastatic). A protein within a cell could also interfere with the replication of a virus.

The delivered polynucleotide can stay within the cytoplasm or nucleus apart from the endogenous genetic material. Alternatively, the polynucleotide could recombine (become a part of) the endogenous genetic material. For example, DNA can insert into chromosomal DNA by either homologous or non-homologous recombination.

Parenchymal cells are the distinguishing cells of a gland or organ contained in and supported by the connective tissue framework. The parenchymal cells typically perform a function that is unique to the particular organ. The term "parenchymal" often excludes cells that are common to many organs and tissues such as fibroblasts and endothelial cells within the blood vessels.

In a liver organ, the parenchymal cells include hepatocytes, Kupffer cells and the epithelial cells that line the biliary tract and bile ductules. The major constituent of the liver parenchyma are polyhedral hepatocytes (also known as hepatic cells) that presents at least one side to an hepatic sinusoid and apposed sides to a bile canaliculus. Liver cells that are not parenchymal cells include cells within the blood vessels such as the endothelial cells or fibroblast cells.

In striated muscle, the parenchymal cells include myoblasts, satellite cells, myotubules, and myofibers. In cardiac muscle, the parenchymal cells include the myocardium also known as cardiac muscle fibers or cardiac muscle cells and the cells of the impulse connecting system such as those that constitute the sinoatrial node, atrioventricular node, and atrioventricular bundle.

In a pancreas, the parenchymal cells include cells within the acini such as zymogenic cells, centroacinar cells, and basal or basket cells and cells within the islets of Langerhans such as alpha and beta cells.

In spleen, thymus, lymph nodes and bone marrow, the parenchymal cells include reticular cells and blood cells (or precursors to blood cells) such as lymphocytes, monocytes, plasma cells and macrophages.

In the nervous system which includes the central nervous system (the brain and spinal cord) peripheral nerves, and ganglia, the parenchymal cells include neurons, glial cells, microglial cells, oligodendrocytes, Schwann cells, and epithelial cells of the choroid plexus.

In the kidney, parenchymal cells include cells of collecting tubules and the proximal and distal tubular cells. In the prostate, the parenchyma includes epithelial cells.

In glandular tissues and organs, the parenchymal cells include cells that produce hormones. In the parathyroid glands, the parenchymal cells include the principal cells (chief cells) and oxyphilic cells. In the thyroid gland, the parenchymal cells include follicular epithelial cells and parafollicular cells. In the adrenal glands, the parenchymal cells include the epithelial cells within the adrenal cortex and the polyhedral cells within the adrenal medulla.

In the parenchyma of the gastrointestinal tract such as the esophagus, stomach, and intestines, the parenchymal cells include epithelial cells, glandular cells, basal, and goblet cells.

In the parenchyma of lung, the parenchymal cells include the epithelial cells, mucus cells, goblet cells, and alveolar cells.

In fat tissue, the parenchymal cells include adipose cells or adipocytes. In the skin, the parenchymal cells include the epithelial cells of the epidermis, melanocytes, cells of the sweat glands, and cells of the hair root.

In cartilage, the parenchyma includes chondrocytes. In bone, the parenchyma includes osteoblasts, osteocytes, and osteoclasts.

An intravascular route of administration enables a polynucleotide to be delivered to parenchymal cells more evenly distributed and more efficiently expressed than direct parenchymal injections.

Intravascular herein means within a hollow tubular structure called a vessel that is connected to a tissue or organ within the body. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein.

Polypeptide refers to a linear series of amino acid residues connected to one another by peptide bonds between the alpha-amino group and carboxy group of contiguous amino acid residues. Protein refers to a linear series of greater than 50 amino acid residues connected one to another as in a polypeptide.

Vectors are polynucleic molecules originating from a virus, a plasmid, or the cell of a higher organism into which another nucleic fragment of appropriate size can be integrated without loss of the vectors capacity for self-replication; vectors introduce foreign DNA into host cells, where it can be reproduced. Examples are plasmids, cosmids, and yeast artificial chromosomes; vectors are often recombinant molecules containing DNA sequences from several sources. A vector includes a viral vector: for example, adenovirus (icosahedral (20-sided) virus that contains; there are over 40 different adenovirus varieties, some of which cause the common cold) DNA; adenoassociated viral vectors (AAV) which are derived from adenoassociated viruses and are smaller than adenoviruses; and retrovirus (any virus in the family Retroviridae that has RNA as its nucleic acid and uses the enzyme reverse transcriptase to copy its genome into the DNA of the host cell's chromosome; examples include VSV G and retroviruses that contain components of lentivirus including HIV type viruses).

Afferent blood vessels of organs are defined as vessels which are directed towards the organ or tissue and in which blood flows towards the organ or tissue under normal physiologic conditions. Conversely, the efferent blood vessels of organs are defined as vessels which are directed away from the organ or tissue and in which blood flows away from the organ or tissue under normal physiologic conditions. In the liver, the hepatic vein is an efferent blood vessel since it normally carries blood away from the liver into the inferior vena cava. Also in the liver, the portal vein and hepatic arteries are afferent blood vessels in relation to the liver since they normally carry blood towards the liver.

B. Delivery of Polynucleotides

In a preferred embodiment of the present invention, a naked polynucleotide is delivered into a liver blood vessel at distal or proximal points. A liver blood vessel includes the portal venous system which transports blood from the gastrointestinal tract and other internal organs (e.g. spleen, pancreas and gall bladder) to the liver. Another liver blood vessel is the hepatic vein. The hepatic vein may also be reached via the inferior vena cava or another blood vessel that ultimately connects to the liver. A needle or catheter is used to inject the polynucleotide into the vascular system. The injection can be performed under direct observation following an incision and visualization of the tissues blood vessels. Alternatively, a catheter can be inserted at a distant site and threaded so that it resides in the vascular system that connects with the target tissue. In another embodiment, the injection could be performed by using a needle that traverses the intact skin and enters a vessel that supplies or drains from the target tissue.

In a preferred embodiment, the liver and portal vein of mice (25 g, 6-week old ICR mice) are visualized through a ventral midline incision. Anesthesia was obtained from intramuscular injections of 1000 μg of ketamine-HCl (Parke-Davis, Morris Plains, N.J.) in 1 ml of normal saline and methoxyflurane (Pitman-Moore, Mudelein, Ill. USA) which was administered by inhalation as needed. Plasmid DNA in 1 ml of various solutions containing heparin to prevent clotting was injected into the portal vein using a needle over approximately 30 sec. At various times after the injection, the animals were sacrificed by cervical dislocation and the livers (average weight of 1.5 g) were divided into six sections composed of two pieces of median lobe, two pieces of left lateral lobe, the right lateral lobe, and the caudal lobe plus a small piece of right lateral lobe. Each of the six sections were placed separately into an homogenizing buffer. The homogenates were centrifuged and the supernatant analyzed for the foreign gene product. If the gene product is secreted then blood is obtained from the retroorbital venous sinus and the level of the secreted protein is assayed in the blood. For example, the expression of the human growth hormone gene can be detected by measuring the amount of human growth hormone in the mouse serum using a radioimmune assay (RIA) (HGH-TGES 100T kit from Nichols Institute, San Juan Capistrano, Calif., USA). Alternatively, the foreign gene could produce an enzyme that corrects an abnormality in the disease state. For example, the phenylalanine hydroxylase gene could be used to normalize the elevated phenylalanine blood levels in a genetic mouse model of phenylketonuria.

In the liver, the hepatic vein is an efferent blood vessel since it normally carries blood away from the liver into the inferior vena cava. Also in the liver, the portal vein and hepatic arteries are afferent blood vessels in relation to the liver since they normally carry blood towards the liver. In a preferred embodiment, plasmid DNA may be efficiently expressed if delivered by a retrograde route into the efferent vessel of the liver (i.e. the hepatic vein). As demonstrated in the examples that follow, injections were directed into the inferior cava which was clamped in two locations; proximal and distal to the entry of the hepatic vein into the inferior vena cava. Specifically, the downstream inferior vena cava clamp was placed between the diaphragm and the entry point of the hepatic vein. The upstream inferior vena cava clamp was placed just upstream of the entry point of the renal veins. Since the veins of other organs such as the renal veins enter the inferior vena cava at this location, not all of the injection fluid went into the liver. In some of the animals that received retrograde injections in the inferior vena cava, the hepatic artery, mesenteric artery, and portal vein were clamped (occluded).

C. Permeability

The efficiency of the polynucleotide delivery and expression was increased substantially by increasing the permeability of a blood vessel within the target tissue. Permeability is defined here as the propensity for macromolecules such as polynucleotides to move through vessel walls and enter the extravascular space. One measure of permeability is the rate at which macromolecules move through the vessel wall and out of the vessel. Another measure of permeability is the lack of force that resists the movement through the vessel wall and out of the vessel. Vessels contain elements that prevent macromolecules from leaving the intravascular space (internal cavity of the vessel). These elements include endothelial cells and connective material (e.g. collagen). Increased permeability indicates that there are fewer of these elements that can block the egress of macromolecules and that the spaces between these elements are larger and more numerous. In this context, increased permeability enables a high percentage of polynucleotides being delivered to leave the intravascular space; while low permeability indicates that a low percentage of the polynucleotides will leave the intravascular space.

The permeability of a blood vessel can be increased by increasing the intravascular hydrostatic pressure. In a preferred embodiment, the intravascular hydrostatic pressure is increased by rapidly (from 10 seconds to 30 minutes) injecting a polynucleotide in solution into the blood vessel which increases the hydrostatic pressure. In another preferred embodiment, hydrostatic pressure is increased by obstructing the outflow of the injection solution from the tissue for a period of time sufficient to allow delivery of a polynucleotide. Obstructing means to block or impede the outflow of injection fluid, thereby transiently (reversibly) blocking the outflow of the blood. Furthermore, rapid injection may be combined with obstructing the outflow in yet another preferred embodiment. For example, an afferent vessel supplying an organ is rapidly injected and the efferent vessel draining the tissue is ligated transiently. The efferent vessel (also called the venous outflow or tract) draining outflow from the tissue is also partially or totally clamped for a period of time sufficient to allow delivery of a polynucleotide. In the reverse, an efferent is injected and an afferent vessel is occluded.

In another preferred embodiment, the intravascular pressure of a blood vessel is increased by increasing the osmotic pressure within the blood vessel. Typically, hypertonic solutions containing salts such as NaCl, sugars or polyols such as mannitol are used. Hypertonic means that the osmolality of the injection solution is greater than physiologic osmolality. Isotonic means that the osmolality of the injection solution is the same as the physiological osmolality (the tonicity or osmotic pressure of the solution is similar to that of blood). Hypertonic solutions have increased tonicity and osmotic pressure similar to the osmotic pressure of blood and cause cells to shrink.

The permeability of the blood vessel can also be increased by a biologically-active molecule in another preferred embodiment. A biologically-active molecule is a protein or a simple chemical such as histamine that increases the permeability of the vessel by causing a change in function, activity, or shape of cells within the vessel wall such as the endothelial or smooth muscle cells. Typically, biologically-active molecules interact with a specific receptor or enzyme or protein within the vascular cell to change the vessel's permeability. Biologically-active molecules include vascular permeability factor (VPF) which is also known as vascular endothelial growth factor (VEGF). Another type of biologically-active molecule can also increase permeability by changing the extracellular connective material. For example, an enzyme could digest the extracellular material and increase the number and size of the holes of the connective material.

EXAMPLES

The following examples are intended to illustrate, but not limit, the present invention.

Example 1

Intraportal Injections of Plasmid DNA:

Methods:

After the livers of 25 g, 6-week old mice were exposed through a ventral midline incision, solutions containing pBS.CMVLux plasmid DNA (described below) were manually injected over approximately 30 sec into the portal vein using a 30-gauge, ½-inch needle and 1-ml syringe. In some animals, a 5×1 mm, Kleinert-Kutz microvessel clip (Edward Weck, Inc., Research Triangle Park, N.C.) was applied during the injection at the junction of the hepatic vein and caudal vena cava. Anesthesia was obtained from intramuscular injections of 1000 μg of ketamine-HCl (Parke-Davis, Morris Plains, N.J.) in 1 ml of normal saline and methoxyflurane (Pitman-Moore, Mudelein, Ill. USA) which was administered by inhalation as needed was purchased from Sigma. Heparin was purchased from LyphoMed (Chicago, Ill.).

Reporter Genes and Assays

The pBS.CMVLux, plasmid DNA was used to express luciferase from the human immediate early cytomegalovirus (CMV) promoter (I. Danko, et al., Gene Therapy 1, 114 (1994) incorporated herein by reference). At two days after injection, the livers were assayed for luciferase expression as previously reported (J. A. Wolff, et al., Science 247, 1465 (1990)) except modified as below. The animals were sacrificed by cervical dislocation and the livers (average weight of 1.5 g) were divided into six sections composed of two pieces of median lobe, two pieces of left lateral lobe, the right lateral lobe, and the caudal lobe plus a small piece of right lateral lobe. Each of the six sections were placed separately into 200 µl of lysis buffer (0.1% Triton X-100, 0.1M K-phosphate, 1 mM DTT pH 7.8) that was then homogenized using a homogenizer PRO 200 (PRO Scientific Inc., Monroe Conn.). The homogenates were centrifuged at 4,000 rpm for 10 min. at 4° C. and 200 µl of the supernatant were analyzed for luciferase activity. Relative light units (RLU) were converted to pg of luciferase using standards from Analytic Luminescence Laboratories (ALL, San Diego, Calif.). Luciferase protein (pg)=$5.1\times10^{-5}\times$RLU+3.683 ($r^2$=0.992). Total luciferase/liver was calculated by adding all the sections of each liver and multiplying by 23 to account for dilution effects. For each condition, the mean total luciferase/liver and the associated standard deviation are shown.

Results:

After the livers of 25 g, 6-week old mice were exposed through a ventral midline incision, 100 µg of pBS.CMVLux, plasmid DNA in 1 ml of solutions was injected into the portal vein via a 30-gauge, ½-inch needle over approximately 30 sec. Two days after injection, a mean of only 0.4 ng of total luciferase/liver was produced when the DNA was delivered intraportally in an isotonic solution without ligation of the hepatic vein (Table 1). Inclusion of 20% mannitol in the injection solution increased the mean total luciferase/liver over ten-fold to 4.8 ng (Table 1).

In order to prevent the DNA's rapid transit and to increase the intraportal hydrostatic pressure, the hepatic vein was clamped for two min after injection. Luciferase production increased another three-fold to 14.7 ng (Table 1).

When the DNA was injected in a hypertonic solution containing 0.9% saline, 15% mannitol and 2.5 units/ml of heparin to prevent microvascular thrombosis and with the hepatic vein clamped, luciferase expression increased eight-fold to 120.3 ng/liver (Table 1). These results are also shown in Table 7 (no dexamethasone condition) in Example 3 below for each individual animal. If the mannitol was omitted under these conditions, luciferase expression was ten-fold less (Table 1).

These results indicate that hypertonicity, heparin and hepatic vein closure are required to achieve very high levels of luciferase expression.

TABLE 1

Mean total luciferase in the liver following the intraportal injection (over 30 seconds) of 100 µg pBS.CMVLux in 1 ml of different solutions with no clamp or with the hepatic vein and inferior vena cava clamped for two minutes.

| Condition | Mean Luciferase (total ng/liver) | Standard Error | Number of Livers |
|---|---|---|---|
| no clamp, normal saline solution (NSS) | 0.4 | 0.7 | n = 6 |
| no clamp, 20% mannitol | 4.8 | 8.1 | n = 3 |
| clamp, 20% mannitol | 14.6 | 26.3 | n = 9 |
| clamp, 2.5 units heparin/ml in NSS | 11.8 | 12.5 | n = 4 |
| clamp, 15% mannitol and 2.5 units heparin/ml in NSS | 120.3 | 101.5 | n = 12 |

Luciferase activities in each liver were evenly distributed in six divided sections assayed (Table 2). All six parts of each liver from all three animals had substantial amounts of luciferase. This is in marked contrast to the direct interstitial, intralobar injection of DNA in which the expression is restricted to the site of injection (R. W. Malone et al., J. Biol. Chem 269, 29903 (1994); M. A. Hickman, et al., Hum. Gene Ther. 5, 1477 (1994) incorporated herein by reference).

TABLE 2

The distribution of luciferase expression over the six liver sections in animals injected intraportally (over 30 seconds) with 100 µg of pBS.CMVLux in 1 ml of normal saline solution plus 15% mannitol and 2.5 units heparin/ml and with the hepatic vein clamped for 2 minutes.

| Liver Section | Total luciferase/Liver (ng/Liver/mouse) | | |
|---|---|---|---|
| | Mouse #1 | Mouse #2 | Mouse #3 |
| ½ of median lobe | 496.5 | 66.9 | 304.5 |
| other ½ of median lobe | 177.0 | 126.1 | 241.4 |
| ½ of left lateral lobe | 763.8 | 208.7 | 325.2 |
| other ½ of left lateral lobe | 409.4 | 160.4 | 218.9 |
| right lateral lobe | 527.8 | 129.7 | 216.2 |
| caudal lobe + small piece of right lateral lobe | 374.1 | 149.7 | 240.8 |
| Total | 2,748.6 | 841.5 | 1,547.0 |
| Mean | 458.1 | 140.3 | 257.8 |
| Range | 177–763 | 67–209 | 216–325 |
| Standard Deviation | 194.0 | 46.6 | 45.9 |

Conclusions:

1. High levels of luciferase expression were obtained from injecting 100 µg of pBS.CMVLux intraportally.

2. The highest levels of luciferase expression were obtained when the animals were injected intraportally over 30 seconds with 100 µg of pBS.CMVLux in 1 ml of normal saline solution plus 15% mannitol and 2.5 units heparin/ml and with the hepatic vein clamped for 2 minutes.

3. These high levels of expression were consistently obtained in dozens of mice.

4. The luciferase expression was evenly distributed throughout the liver.

Example 2

The effects of other factors on expression were explored using the same methods for the intraportal injection of pBS.CMVLux.

Methods:

Unless otherwise specified, the intraportal injections and luciferase assays were done as in Example 1.

Results:

Compared to the results with 100 µg of pBS.CMVLUX, luciferase expression was not greater with 500 µg of plasmid DNA (Table 3). Luciferase expression was approximately 7-fold less if 20 µg of pBS.CMVLux DNA was injected instead of 100 µg.

TABLE 3

Total luciferase expression in each liver of each animal injected intraportally (over 30 sec) with 20 µg, 100 µg, or 500 µg of pBS.CMVLux in 1 ml of normal saline solution plus 15% mannitol and 2.5 units heparin/ml and with the hepatic vein occluded for 2 min.

| | Total luciferase/Liver (ng/Liver/mouse) | |
|---|---|---|
| Mouse Number | 100 µg pBS.CMVLux | 500 µg pBS.CMVLux |
| 1 | 1,023 | 15 |
| 2 | 178 | 82 |
| 3 | 108 | 23 |
| 4 | 140 | 340 |
| Mean | 362 | 115 |
| Standard Deviation | 441 | 153 |

The times for which the hepatic vein was occluded were varied from 2 min to 4 min and to 6 min. In Table 4, one can see that the time of occlusion did not have a large effect on expression.

TABLE 4

Effect of time of hepatic vein occlusion on luciferase expression in animals injected intraportally with 100 µg of pBS.CMVLux in 1 ml of normal saline solution plus 15% mannitol and 2.5 units heparin/ml.

| | Total luciferase/Liver (ng/Liver/mouse) | | |
|---|---|---|---|
| Mouse Number | 2 min | 4 min | 6 min |
| 1 | 4.6 | 1.9 | 32.7 |
| 2 | 44.9 | 11.5 | 6.4 |

The times over which the injections were done were varied from 30 seconds to 1 minute and 2 minutes. In Table 5, one can see that injecting the 1 ml of the DNA solution (100 µg pBS.CMVLux) over 30 seconds enabled the highest levels of luciferase expression. Longer times of injection led to lower levels.

TABLE 5

Effect of length of injection (time it took to inject all of the 1 ml) on luciferase expression in animals injected intraportally with 100 µg of pBS.CMVLux in 1 ml of normal saline solution plus 15% mannitol and 2.5 units heparin/ml and with the hepatic vein occluded for 2 min.

| | Total luciferase/Liver (ng/Liver/mouse) | | |
|---|---|---|---|
| Mouse Number | 30 sec | 1 min | 2 min |
| 1 | 2,697 | 188 | 21.6 |
| 2 | 790 | 13.4 | 19.9 |
| 3 | 1,496 | 141.1 | 11.8 |
| Mean | 1,662 | 114 | 18 |
| Standard Deviation | 964 | 91 | 5 |

If the total volume of the injection fluid was 0.5 ml instead of 1.0 ml, luciferase expression decreased 70-fold (Table 6) suggesting that 0.5 ml was not sufficient to fill the intravascular space and distribute the DNA throughout the parenchyma.

TABLE 6

Total luciferase expression in each liver of each animal injected intraportally (over 30 sec) with 100 µg of pBS.CMVLux in either 0.5 or 1 ml of normal saline solution plus 15% mannitol and 2.5 units heparin/ml and with the hepatic vein occluded for 2 min.

| | Total luciferase/Liver (ng/Liver/mouse) | |
|---|---|---|
| Mouse Number | 0.5 ml | 1 ml |
| 1 | 1.6 | 51.9 |
| 2 | 4.7 | 124.8 |
| 3 | 0.4 | 266.9 |
| Mean | 2.3 | 147.9 |
| Standard Deviation | 2.3 | 109.4 |

Conclusions:

1. The optimal conditions are in fact the conditions first described in example 1: the animals were injected intraportally over 30 seconds with 100 µg of pBS.CMVLux in 1 ml of normal saline solution plus 15% mannitol and 2.5 units heparin/ml and with the hepatic vein clamped for 2 minutes.

2. Use of 500 µg of pBS.CMVLux did not enable greater levels of expression but expression was approximately7-fold less if 20 µg of DNA was used.

3. Occluding the hepatic vein for longer than 2 minutes did not increase expression.

4. Injecting the pBS.CMVLux over 30 seconds gave the highest luciferase levels as compared to injection times longer than 30 seconds.

5. Injecting the pBS.CMVLux in 1 ml gave higher luciferase levels than injecting the pBS.CMVLux in 0.5 ml.

Example 3

Methods:

The intraportal injections and luciferase assays were performed as in Example 1 except that some animals received daily subcutaneous injections of 1 mg/kg of dexamethasone (Elkins-Sinn, Cherry Hill, N.J.) starting one day prior to surgery. The conditions for the injections were intraportal injections over 30 seconds with 100 µg of pBS.C-

MVLux in 1 ml of normal saline solution plus 15% mannitol and 2.5 units heparin/ml and with the hepatic vein clamped for 2 minutes.

Results:

Under the conditions described above (i.e., hypertonic solution containing heparin and hepatic vein closure) into animals that had been injected with daily injections of dexamethasone starting the day prior to plasmid injection, luciferase expression was three-fold greater than the expression without dexamethasone (Table 7).

TABLE 7

The effect of dexamethasone injections on luciferase expression after the intraportal injection of pBS.CMVLux.

| | Total luciferase/Liver (ng/Liver/mouse) | |
|---|---|---|
| Mouse Number | NO Dexamethasone | WITH Dexamethasone |
| 1 | 51.9 | 1,181.1 |
| 2 | 124.8 | 364.7 |
| 3 | 266.9 | 82.8 |
| 4 | 73.7 | 120.5 |
| 5 | 52.6 | 1,022.9 |
| 6 | 7.3 | 178.1 |
| 7 | 146.1 | 107.6 |
| 8 | 231.4 | 140.2 |
| 9 | 271.2 | |
| 10 | 8.7 | |
| 11 | 8.3 | |
| 12 | 201.1 | |
| Mean | 120.3 | 399.8 |
| Standard Deviation | 101.4 | 444.1 |

Dexamethasone could have increased the production of luciferase and the expression of other genes by several mechanisms. They include increasing the amount of plasmid DNA that enters the liver cells by modifying the state of the liver cells. It could also help the liver cells withstand the increased pressure. However, the most likely mechanism is that dexamethasone directly stimulates the CMV promoter and thereby directly increases expression of luciferase by stimulating transcription of the luciferase messenger RNA.

The use of dexamethasone demonstrates that using a readily available pharmaceutical, the levels of expression can be substantially increased and regulated.

Conclusion:

1. Dexamethasone administration increased luciferase expression from intraportally-injected pBS.CMVLux plasmid DNA three-fold.

2. This demonstrates that the expression from the liver can be regulated using a commonly-used pharmaceutical.

Example 4

Methods:

The intraportal injections were performed using the previously stated technique of injections over 30 seconds with 100 μg of plasmid DNA in 1 ml of normal saline solution plus 15% mannitol and 2.5 units heparin/ml and with the hepatic vein clamped for 2 minutes. The mice also received daily subcutaneous injections of 1 mg/kg of dexamethasone (Elkins-Sinn, Cherry Hill, N.J.) starting one day prior to surgery.

The plasmids pBS.CMVLacZ and pBS.CMVnLacZ were used to express a cytoplasmic and nuclear β-galactosidase protein, respectively, from the CMV promoter (Picard, D. & Yamamoto, K. EMBO J. 6:3333–3340, 1987; incorporated herein by reference). They were constructed by placing either a 3.5-kg-HindIII/XbaI B-galactosidase sequence from pSDKLacZpa (Danko, I. et al. Gene Therapy 1:114–121, 1994; incorporated herein by reference) or a sequence encoding a nuclear-localizing -galactosidase (Picard, D. & Yamamoto, K. EMBO J. 6:3333–3340, 1987; incorporated herein by reference) into pBlueCMV (Danko, I. et al. Gene Therapy 1: 114–121, 1994; incorporated herein by reference).

Two days after intraportal injection, the livers were perfused with 1% paraformaldehyde and 1.25% glutaraldehyde in phosphate buffered saline (PBS) and then kept in this solution for one day. After the livers were stored in 30% sucrose, they were cryosectioned. The sections were mounted on slides and stained for 1 hour to one day with a PBS solution (pH 7.5) containing 400 μg/ml X-gal (5-bromo-4-chloro-3-indolyl-β-D-galactoside) (Sigma), 5 mM potassium ferricyanide, 5 mM ferrocyanide, and 1 mM $MgCl_2$. After washing, the sections were then counterstained with hematoxylin and eosin. In the livers injected with the nuclear-localizing β-galactosidase vector, the washing step after hematoxylin incubation was omitted to decrease its nuclear staining.

Results:

Having defined the optimal conditions, the types and percentages of transfected cells were determined. After injections of a 100 μg of the cytoplasmic (pBS.CMVLacZ) or the nuclear (pBS.CMVnLacZ) β-galactosidase expression vectors into dexamethasone-treated animals, liver cryosections 10- to 30-μm thick were stained for β-galactosidase using X-gal at pH 7.5 to prevent background staining. Intense blue staining was observed in approximately 1% of the liver cells and was evenly distributed throughout the liver. X-gal incubations for only 1 hour resulted in intensely blue cells; suggesting that the transfected cells expressed relatively large amounts of the foreign genes. Control livers injected with 100 μg of pBS.CMVLux did not contain any positively-stained cells. Necrosis was observed in approximately 10% of the sections. However, some livers with high β-galactosidase expression did not contain any sections with necrosis.

The hepatocytes were identified by their characteristic morphology. For example, many of the cells in the livers injected with the nuclear β-galactosidase vector, pBS.CMVnLacZ, had blue staining in two nuclei, which is a trait only of hepatocytes. Although the majority of the positively-stained cells were hepatocytes a few small, non-hepatocyte cells contained blue staining.

Conclusion:

1. Approximately 1% of the liver cells were transfected with the B-galactosidase gene throughout the entire liver.

2. Almost all of the transfected liver cells were hepatocytes.

Example 5

Methods:

Luciferase expression in the liver was compared to that in cultured HepG2 hepatocytes in 35-mm plates. Transfections were done using 3 μg of pBS.CMVLux/plate and either 3 μg of Lipofectin (Life Technologies, Bethesda, Md.) or 6 μg of LipofectAMINE (Life Technologies, Bethesda, Md.) per manufacturer's instructions. Two days after transfection, 200 ul of lysis buffer was added to the cultures and 20 ul of the supernatant were analyzed for luciferase activity as in Example 1.

Results:

The efficiency of luciferase expression using this technique was compared to other methods of gene transfer both in vitro and in vivo. Transfections performed under optimal conditions with pBS.CMVLUX and Lipofectin or LipofectAMINE (Life Technologies Inc.) in HepG2 hepatocytes in culture (n=8) yielded a mean total of 3.7±4.5 ng luciferase/35-mm plate and 2.8±2.0 ng luciferase/35-mm plate. Thus the efficiency of transfection (without dexamethasone) in terms of ng of luciferase/µg of pBS.CMVLUX DNA was approximately 1 ng/µg both in vitro and in vivo.

The published procedure of repetitively and directly injecting naked plasmid DNA into a rat liver lobe was reduced proportionately for mouse liver (R. W. Malone et al., J. Biol. Chem 269, 29903 (1994); M. A. Hickman, et al., Hum. Gene Ther. 5, 1477 (1994); incorporated herein by reference). A total of 100 µg of pBS.CMVLUX in a total volume of 200 ul of normal saline was injected within five different sites (40 ul/site) into the left lateral lobe of 30 g mice treated with dexamethasone. A mean total of only 0.1 ng/liver (4 livers; 0.001 ng luciferase/µg DNA) was obtained and the luciferase expression was only present in the injected lobe. Approximately 30-fold more luciferase expression was obtained if the direct intralobar injections were done using 1 ml of injection fluid and clamping the hepatic vein. In the previous studies involving the multiple injections of a total of 500 µg of pCMVL into a liver lobe of dexamethasone-treated rats, a mean of 9.87 ng of luciferase/liver (0.02 ng/µg DNA) was expressed (R. W. Malone et al., *J. Biol. Chem* 269, 29903 (1994); M. A. Hickman, et al., *Hum. Gene Ther.* 5, 1477 (1994)).

With regard to muscle, we typically inject 10 µg of pBS.CMVLUX or pBS.RSVLUX ((Danko, I. et al. Gene Therapy 1:114–121, 1994)) in normal saline into 6–8 mouse quadriceps muscle per experiment. In dozens of experiments, mean total luciferase per muscle was 0.4–1 ng (±0.5–1.2) and the efficiency was 0.04–0.1 ng luciferase/µg DNA.

TABLE 8

Comparison of efficiency of gene transfer in terms of luciferase expressed per µg of pBS.CMVLux plasmid DNA used for the method (ng luciferase/µg DNA).

| Method of Gene Transfer | Mean Total Yield Of Luciferase (ng) | Amount of pBS. CMVLux Used (µg) | Efficiency (ng Luciferase/ µg DNA) |
| --- | --- | --- | --- |
| Intraportal Mouse Liver (above optimal conditions- Table 1) hepatic vein clamped | 120.3 ± 101.5 n = 12 | 100 | 1.2 |
| HepG2 In Vitro with Lipofectin | 3.7 ± 4.5 (n = 8) | 3 | 1.2 |
| HepG2 In Vitro with LipofectAMINE | 2.8 ± 2.0 (n = 8) | 3 | 0.9 |
| Intralobar Mouse Liver (20 ul/site × 5 sites) hepatic vein not clamped | 0.1 ± 0.1 n = 4 | 100 | 0.001 |
| Intralobar Mouse Liver (1 ml/1 site) hepatic vein clamped | 2.8 ± 5.6 n = 4 | 100 | 0.028 |
| Intralobar Rat Liver (5 sites) from published data (Journal of Biologic Chemistry 269: 29903, 1994; Human Gene Therapy 5: 1477, 1994) | 9.87 | 500 | 0.02 |
| Intramuscular | 0.4–1 ± 0.5–1.2 n > 50 | 10 | 0.04–0.1 |

Conclusions:

1. The intraportal delivery of naked DNA was more than an order of magnitude more efficient than interstitial delivery into either liver or muscle and more evenly distributed.

Example 6

Methods:

The intraportal injections were done using the above optimal injections which are intraportal injections over 30 seconds with 100 µg of pCMVGH in 1 ml of normal saline solution plus 15% mannitol and 2.5 units heparin/ml and with the hepatic vein clamped for 2 minutes. Some animals received daily intramuscular injections of 100 mg/kg of cyclosporine (Sandimmune, Sandoz) or daily subcutaneous injections of 1 mg/kg of dexamethasone (Elkins-Sinn, Cherry Hill, N.J.), or both starting one day prior to surgery.

The previously described pCMVGH plasmid DNA was used to express human growth hormone (hGH) (C. Andree, et al., Proc. Natl. Acad. Sci. U.S.A. 91, 12188 (1994); incorporated herein by reference). Blood obtained from the retro-orbit sinus was analyzed for serum concentration of hGH using the radioimmune assay (RIA), HGH-TGES 100T kit from Nichols Institute (San Juan Capistrano, Calif.).

Results:

Human growth hormone (hGH) was used as a marker gene to assess the ability of this gene transfer technique to produce a therapeutic serum protein (Table 9). Two days after the intraportal injection of 100 µg of pCMVGH under the above optimal conditions, the mean hGH serum concentration was 57±22 ng/ml (n=12) with a range of 21–95 ng/ml. Neither dexamethasone nor cyclosporine pre-treatment significantly affected these initial hGH levels. In two animals injected with pBS.CMVLUX, background hGH levels were 0.3±0.1 ng/ml for 4 weeks afterwards.

In humans, normal pulsatile levels of GH peak at approximately 20 ng/ml above baseline values of approximately 1 ng/ml and can attain concentrations of 10–180 ng/ml after growth hormone releasing hormone (GHRH) stimulation (A. Favia, J. D. Veldhuis, M. O. Thorner, M. L. Vance, J. Clin. Endocrinol. Metab. 68, 535 (1989); R. W. Holl, M. L. Hartman, J. D. Veldhuis, W. M. Taylor, M. O. Thorner, J. Clin. Endocrinol. Metab. 72, 854 (1991); W. S. Evans et al., Am. J. Physiol. 252, E549 (1987); F. P. Alford, H. W. G. Baker, H. G. Burger, J. Clin Endocrinol. Metab. 37, 515 (1973); incorporated herein by reference). The half-life of hGH is approximately 20 min in humans and 4.5 min in mice; hence these serum levels could translate into much higher levels for more stable proteins (S. Peeters and H. G.

Friesen, Endocrinol. 101, 1164 (1977); A. Favia, J. D. Veldhuis, M. O. Thorner, M. L. Vance, J. Clin. Endocrinol. Metab. 68, 535 (1989); incorporated herein by reference). For example, if a protein such as alpha-antitrypsin has a half-life that is ten times longer than human GH, then the circulating blood levels should be at more than ten times higher given the same efficiency of protein production. Another example is that for hemophilia which requires levels of factor VIII or IX in the range of approximately 1 82 g of the clotting factor/ml of blood. Given the increased stability of these clotting factors, then the 0.1 μg/ml of hGH that we can achieve after intraportal injection of the respective gene means that we would be able to obtain therapeutic levels of clotting factors to prevent bleeding in patients with hemophilia. In summary, these results demonstrate that the intraportal naked DNA technique could be used to produce therapeutic levels of a circulating blood protein.

Serial measurements of hGH serum levels enabled the stability of expression in individual mice to be assessed (Table 9). In untreated animals, hGH expression was unstable as in previous studies in which the plasmid DNA was delivered to non-hepatectomized livers using polylysine complexes or intralobar injections of naked DNA.

An immune response could kill hepatocytes expressing the human protein. To test the hypothesis that expression was unstable because of an immune response, hGH levels were followed in animals that received cyclosporine with or without dexamethasone administration (Table 9). After an acute drop off, hGH levels remained at 6–11 ng/ml for four weeks in animals that received both dexamethasone and cylcosporine. In animals that received dexamethasone alone or cyclosporine alone, hGH expression was prolonged as compared to the non-treated animals but not to the same extent as the animals that received both agents. The ability for this gene transfer method to enable expression of a foreign gene should increase its utility.

TABLE 9

Mean serum levels (ng/ml of serum) of human growth hormone (hGH) following intraportal administration of pCMVGH under optimal conditions in mice (2 to 3 animals for each timepoint) receiving various treatments. Optimal conditions are defined as the use of 0.9% saline, 15% mannitol, 2.5 units/ml heparin solution that was intraportally injected with the hepatic vein closed.

| DAYS AFTER INJECTION | NONE | CSA alone | DEX alone | CSA + DEX |
|---|---|---|---|---|
| 2 | 69 | 43 | 72 | 51 |
| 4 | 11 | 8 | 14 | 14 |
| 8 | 3 | 6 | 7 | 13 |
| 12 | 0 | 4 | 7 | 15 |
| 15 | 0 | 3 | 5 | 13 |
| 21 | 0 | 1.5 | 2.6 | 9.7 |
| 28 | 0 | 1 | 2.2 | 7.9 |

Conclusions:

1. These results demonstrate that the intraportal naked DNA technique could be used to produce therapeutic levels of a circulating blood protein that is currently used to treat humans.

2. The levels of the circulating blood protein (i.e. hGH) remained elevated for at least one month after a single injection.

Example 7

Methods:

After the portal veins of 25 g, 6-week old mice were exposed through a ventral midline incision, 100 μg of pBS.CMVLux plasmid DNA in 0.5 ml or 1 ml of normal saline solution plus 15% mannitol and 2.5 units heparin/ml were manually injected over 30 seconds into the portal vein near the junction of the splenic vein and portal vein. The portal vein had two clamps placed distal and proximal to the point of injection so as to direct the injection fluid into only the splenic vein and to prevent the injection fluid from going to the liver or intestines. The injections were done using a 30-gauge, ½-inch needle and 1-ml syringe. 5×1 mm, Kleinert-Kutz microvessel clips (Edward Weck, Inc., Research Triangle Park, N.C.) were used. Anesthesia was obtained from intramuscular injections of 1000 μg of ketamine-HCl (Parke-Davis, Morris Plains, N.J.) and methoxyflurane (Pitman-Moore, Mudelein, Ill. USA) which was administered by inhalation as needed was purchased from Sigma. Heparin was purchased from LyphoMed (Chicago, Ill.).

Two days after injection the spleens and pancreas were removed and placed in 500 ul of lysis buffer and 20 ul were analyzed for luciferase expression as described above.

Results:

Substantial amounts of luciferase activity were obtained in the spleen and pancreas of all four mice with both injection fluids of 0.5 ml and 1 ml.

TABLE 10

Luciferase expression after the intravascular-administration of pBS.CMVLux into the splenic vein via the portal vein.

| | Total luciferase/Organ (pg/organ/mouse) | |
|---|---|---|
| Injection Volume | Spleen | Pancreas |
| 0.5 ml | 814.4 | 97.2 |
| 0.5 ml | 237.3 | 88.7 |
| 1 ml | 168.7 | 109.4 |
| 1 ml | 395.0 | 97.7 |
| Mean | 403.9 | 98.3 |
| Standard Deviation | 289.6 | 8.5 |

Conclusion:

1. Intravascularly-administered plasmid DNA can express efficiently in spleen and pancreas.

Example 8

Methods:

100 μg of pBS.CMVLux in 10 ml of normal saline solution plus 15% mannitol was injected into the femoral artery of adult rats with the femoral vein clamped. One to four days after injection, the quadricep was removed and cut into 10 equal sections. Each sections were placed into 500 ul of lysis buffer and 20 ul were assayed for luciferase activity as described above.

Results:

Substantial amounts of luciferase expression were expressed in the quadriceps following the intravascular delivery of plasmid DNA.

TABLE 11

Luciferase expression in the quadricep of a rat after
the injection of 100 µg of pBS.CMVLux into the
femoral artery and with the femoral vein clamped.

| Rat Number | Total Luciferase (pg/quadriceps) |
|---|---|
| 1 | 157.5 |
| 2 | 108.8 |
| 3 | 139.2 |
| 4 | 111.3 |
| Mean | 129.2 |
| Standard Deviation | 23.4 |

Conclusion:

1. Intravascularly-administered plasmid DNA can express efficiently in muscle.

Example 9

The previous examples involved injections into the afferent blood vessels of organs. In the liver, the hepatic vein is an efferent blood vessel since it normally carries blood away from the liver into the inferior vena cava. Also in the liver, the portal vein and hepatic arteries are afferent blood vessels in relation to the liver since they normally carry blood towards the liver.

These set of experiments were designed to determine whether plasmid DNA could be efficiently expressed if delivered by a retrograde route into the efferent vessel of the liver (i.e. the hepatic vein).

Since another luciferase expression vector was used, pCILuc, the results obtained with the hepatic vein injections were directly compared to results using the above technique of injecting the portal vein.

Methods:

100 µg of pCILuc in 1 ml of normal saline solution plus 15% mannitol and 2.5 units heparin/ml were injected over 30 seconds into hepatic vein via the inferior vena cava. Since it was difficult to directly inject the hepatic vein in rodents, the injections were directed into the inferior cava which was clamped in two locations; proximal and distal (i.e. downstream and upstream) to the entry of the hepatic vein into the inferior vena cava. Specifically, the downstream inferior vena cava clamp was placed between the diaphragm and the entry point of the hepatic vein. The upstream inferior vena cava clamp was placed just downstream of the entry point of the renal veins. Therefore, the 1 ml of the injection fluid entered the hepatic vein and the liver. Since the veins of other organs such as the renal veins enter the inferior vena cava at this location, not all of the 1 ml of injection fluid goes into the liver.

In some of the animals that received retrograde injections in the inferior vena cava, the hepatic artery, mesenteric artery, and portal vein were clamped (occluded) for approximately five minutes immediately before and then after the injections. Specifically, the order of placing the clamps were as follows: first on hepatic artery, then portal vein, then downstream vena cava, and then upstream vena cava. It took about three minutes to place all these clamps and then the injections were done. The clamps were left in place for an additional two minutes from the time that the last clamp (upstream vena cava clamp) was placed.

The intraportal injections were performed as stated using optimal intraportal injections over 30 seconds with 100 µg of pCILuc in 1 ml of normal saline solution plus 15% mannitol and 2.5 units heparin/ml and with the hepatic vein clamped for 2 minutes.

Some of the mice also received daily subcutaneous injections of 1 mg/kg of dexamethasone (Elkins-Sinn, Cherry Hill, N.J.) starting one day prior to surgery.

The pCILuc plasmid expresses a cytoplasmic luciferase from the CMV promoter. It was constructed by inserting the cytoplasmic luciferase CDNA into the pCI (Promega Corp., Madison, Wis.) CMV expression vector. Specifically, a NheI/EcoRI restriction digestion fragment containing the cytoplasmic luciferase cDNA was obtained from pSPLuc (Promega Corp.) and inserted into pCI plasmid DNA that was digested with NheI and EcoRI, using conventional recombinant DNA techniques (Sambrook, J., Fritsch, E. F., and Maniatis, T. (1989) in Molecular Cloning Cold Spring Harbor Laboratory Press, Cold Spring Harbor, N.Y.).

Two days after the injections, the luciferase activity was measured as above in six liver sections composed of two pieces of median lobe, two pieces of left lateral lobe, the right lateral lobe, and the caudal lobe plus a small piece of right lateral lobe.

Results:

A. Inferior Vena Cava/Hepatic Vein Injections with the Portal Vein and Hepatic Artery Clamped (*Injections in animal #3 were not optimal since the fluid leaked during the injections.) Injections were done in 6-week old animals that received dexamethasone.

| Sections | Luciferase Activity (ng) | | |
|---|---|---|---|
| | Animal #1 | Animal #2 | Animal #3* |
| 1 | 5,576.7 | 4,326.4 | 1,527.4 |
| 2 | 8,511.4 | 4,604.2 | 1,531.6 |
| 3 | 5,991.3 | 5,566.1 | 2,121.5 |
| 4 | 6,530.4 | 9,349.8 | 1,806.3 |
| 5 | 8,977.2 | 4,260.1 | 484.2 |
| 6 | 9,668.6 | 6,100.2 | 1,139.3 |
| total liver | 45,255.5 | 34,206.9 | 8,610.4 |
| Mean | 29,357.6 | | |
| standard deviation | 18,797.7 | | |

B. Inferior Vena Cava/Hepatic Vein Injections with the Portal Vein and Hepatic Artery not Clamped. Injections were done in 6-week old animals that did not receive dexamethasone.

| Sections | Luciferase Activity (ng) | |
|---|---|---|
| | Animal #1 | Animal #2 |
| 1 | 360.6 | 506.2 |
| 2 | 413.5 | 724.7 |
| 3 | 463.0 | 626.0 |
| 4 | 515.5 | 758.6 |
| 5 | 351.6 | 664.8 |
| 6 | 437.8 | 749.6 |
| total liver | 2,542.0 | 4,029.8 |
| Mean | 3,285.9 | |
| standard deviation | 1,052.1 | |

C. Portal Vein Injections with the Hepatic Vein Clamped in 6 month old mice that received dexamethasone.

| | Luciferase Activity (ng) | | |
|---|---|---|---|
| Sections | Animal #1 | Animal #2 | Animal #3 |
| 1 | 287.4 | 417.0 | 129.2 |
| 2 | 633.7 | 808.1 | 220.5 |
| 3 | 689.8 | 1,096.5 | 328.2 |
| 4 | 957.8 | 1,056.9 | 181.6 |
| 5 | 660.7 | 1,487.4 | 178.6 |
| 6 | 812.4 | 1,276.4 | 233.4 |
| total liver | 4,041.8 | 6,142.2 | 1,271.5 |
| Mean | 3,818.5 | | |
| standard deviation | 2,443.0 | | |

D. Portal Vein Injections with the Hepatic Vein Clamped in 6 week old mice that received dexamethasone.

| | Luciferase Activity (ng) | | |
|---|---|---|---|
| Sections | Animal #1 | Animal #2 | Animal #3 |
| 1 | 352.9 | 379.1 | 87.0 |
| 2 | 667.5 | 373.9 | 108.2 |
| 3 | 424.8 | 1,277.9 | 178.4 |
| 4 | 496.3 | 1,308.6 | 111.9 |
| 5 | 375.2 | 296.4 | 162.3 |
| 6 | 434.7 | 628.7 | 123.0 |
| total liver | 2,751.4 | 4,264.7 | 770.9 |
| Mean | 2,595.7 | | |
| standard deviation | 1,752.1 | | |

E. Summary Table Comparing the Luciferase Expression Obtained Using the Above Conditions.

| Injection Condition@ | Mean Total Luciferase/Liver (μg/liver) | Times Condition D. |
|---|---|---|
| Condition A | 29.4 | 11.3 X |
| Condition B | 3.3 | 1.27 X |
| Condition C | 3.8 | 1.46 X |
| Condition D | 2.6 | 1.00 X |

Condition A=Inferior Vena Cava/Hepatic Vein Injections with the Portal Vein and Hepatic Artery Clamped in 6 week-old animals that received dexamethasone.
Condition B=Inferior Vena Cava/Hepatic Vein Injections with the Portal Vein and Hepatic Artery not Clamped in 6-week old animals that did not receive dexamethasone.
Condition C=Portal Vein Injections with the Hepatic Vein Clamped in 24 week old mice that received dexamethasone.
Condition D=Portal Vein Injections with the Hepatic Vein Clamped in 6 week old mice that received dexamethasone.

Conclusions:
1. Retrograde delivery of plasmid DNA into the efferent vessels of the liver via the hepatic vein/inferior vena cava leads to high levels of gene expression.
2. The highest levels were achieved using this retrograde approach if the afferent vessels to the liver (portal vein and hepatic artery) were occluded.
3. The ClLuc plasmid enabled much higher levels of luciferase expression than the pBS.CMVLux plasmid (see above examples) using the portal vein approach in both 6-week old and 6-month old mice.
4. Under all conditions, luciferase expression was evenly distributed throughout all six liver sections.

Example 10

Animals that received injections into the inferior vena cava were assayed for luciferase to determine whether retrograde delivery into the efferent vessels (veins) of other organs enable gene expression.

Methods:

In the same animals that were injected using condition A above (Inferior Vena Cava/Hepatic Vein Injections with the Portal Vein and Hepatic Artery Clamped in 6 week-old animals that received dexamethasone), the kidneys were removed and assayed for luciferase as described above.

In the same animals that were injected under condition B above (Inferior Vena Cava/Hepatic Vein Injections with the Portal Vein and Hepatic Artery NOT Clamped in 6-week old animals that did not receive dexamethasone), the adrenal gland and diaphragm muscle, abdominal muscles, and back muscles were removed for luciferase analysis.

Results:
A. Luciferase Activity in Kidneys in Animals Injected Under Condition A.

| | Total Luciferase Activity/ Kidney (pg/kidney) | | |
|---|---|---|---|
| | Animal #1 | Animal #2 | Animal #3* |
| Right Kidney | 10,827.8 | 7,662.3 | 636.3 |
| Left Kidney | 733.1 | 753.8 | 479.7 |

*Injection fluid leaked.

B. Luciferase Activity in Adrenals and Various Muscles Injected Under Condition B.

| | Total Luciferase Activity/ Tissue (pg/tissue) | | |
|---|---|---|---|
| | Animal #7 | Animal #8 | Animal #9 |
| right adrenal | not assayed | 82.0 | 49.9 |
| left adrenal | not assayed | 48.4 | 42.2 |
| Diaphragm | 41.9 | 67.9 | 117.6 |
| Abdomen | 40.4 | 43.9 | 44.0 |
| Back | 37.7 | 40.1 | 40.9 |

Conclusions:
1. Retrograde delivery of plasmid DNA into the efferent vessels of several different tissues led to substantial levels of foreign gene expression in the tissues.
2. These tissues include the adrenal glands (suprarenal glands), the diaphragm muscle, back muscles and abdominal muscles.
3. Foreign gene expression in the diaphragm would be especially useful for Duchennes muscular dystrophy since humans with this disorder die from respiratory failure due to fibrosis of the diaphragm muscle

Example 11

This example explores the use of more accessible vessels such as the hepatic vein and the bile duct, for delivering the naked pDNA in mice. Efficient gene expression was obtained using these efferent delivery routes. Occlusion of other vessels to restrict outflow of the injection solutions enhanced but was not critical for efficient expression. Repetitive injections into the bile duct were also accomplished. Preliminary results are also presented in larger animals, the rat and dog. The incorporation of these findings into laboratory and clinical protocols is discussed.

Materials and Methods:

Plasmid Constructs: The pCILuc plasmid expresses a cytoplasmic luciferase from the human CMV immediately early (hCMV ID) promoter. It was constructed by inserting the luc+ gene, an Nhe I-EcoR I luc+ fragment from pSLuc+ (Promega, Madison, Wis.), into the pCI expression vector (Promega). pCILux expresses peroxisomal luciferase under control of the hCMV IE promoter. It was constructed by inserting the luciferase gene (Hind III-Bam HI fragment from pBlueCMVLux) into the Sma I site of pCI. pCILacZ was constructed by placing the E. coli LacZ gene (Pst I-Apa I fragment pBS-RSV-LacZ) into the pCI vector (Sma I site). The pCMVGH construct was previously described (Andree, et al., 1994).

Injection Methods: Plasmid delivery into the hepatic vessels was performed in 6-week old ICR mice, 2.5–6.25 month-old, 200–300 gram Sprague-Dawley rats, and beagle dogs. Ventral midline incisions were performed to expose the liver and the associated vessels. The mice were anesthetized with intramuscular injections of 1000:g of ketamine-HCl (Parke-Davis, Morris Plains, N.J.) and methoxyflurane (Pitman-Moore, Mudelein, Ill.) which was administered by inhalation as needed. The rats were anesthetized with ether and the dogs were anesthetized with halothane by inhalation. The pDNA was injected in solutions containing 2.5 units/ml or heparin (Lypho-Med, Inc., Chicago, Ill.) (Qian et al., 1991) and either normal saline (0.9% NaCl) or 15% mannitol in normal saline (Sigma Chemical Co., St. Louis, Mo.). All animals received humane care in compliance with institutional (IACUC) guidelines.

In mice, the intraportal injections were performed as previously described (Budker, et al., 1996). 100:g of pDNA in 1 ml were manually injected over ~30 see using a 30-gauge, ½-inch needle and 1-ml syringe without occluding the portal vein upstream from the point of injection. In some animals, a 5×1 mm, Kleinert-Kutz microvessel clip (Edward Week, Inc., Research Triangle Park, N.C.) was applied during the injection at the junction of the hepatic vein and caudal vent cava.

DNA was delivered in mice to the hepatic vein via an occluded IVC. Clamps (6×1 mm, Kleinert-Kutz curved microvessel clip (Edward Week, Inc., Research Triangle Park, N.C.) were applied downstream (toward the heart) of the hepatic vein and upstream (towards the legs) of the hepatic and renal veins. Injections were done upstream of the hepatic vein. In some of the injections, the portal vein and hepatic artery were clamped using 6×1 mm, Kleinert-Kutz curved microvessel clips. The IVC mouse injections were also performed with 100:g of pDNA in 1 ml that were manually injected over ~30 sec with a 30-gauge, ½-inch needle and 1-ml syringe.

The bile duct injections in mice were performed using manual injections with a 30-gauge, ½-inch needle and 1-ml syringe. A 5×1 mm, Kleinert-Kutz microvessel clip was used to occlude the bile duct downstream from the point of injection in order to prevent flow to the duodenum and away from the liver. The gallbladder inlet was not occluded. In some of the bile duct injections, the junction of the hepatic vein and caudal vena cava clamped as above. In yet other injections, the portal vein and hepatic artery were clamped in addition to the occlusion of the hepatic vein.

In mice, repetitive injections into the bile duct were done by placing a polyethylene tube (I.D. 0.28 mm, O.D. 0.61 mm; Intramedic Clay Adams Brand, Becton Dickinson Co., Sparks, Md., USA) catheter into the bile duct after making a hole with a 27 gauge needle. The tubing was secured by a suture around the bile duct and tubing; thereby occluding the bite duct. The other end of the tubing was placed outside the skin of the animal's back so that surgery was not required for repeat injections. No blood vessel occlusions were done for these repetitive administrations. After completion of the studies, anatomical examination indicated that the catheter remained in the bile duct.

In rats, the intraportal, IVC, and bile duct injections were done as in mice but with the following modifications. The injections were done through a 25-g butterfly needle using a peristaltic pump (Preston varistaltic power pump, Manostat Corp., New York, N.Y.) over 1 or 3 minutes. The downstream IVC clamps in the IVC injections were done downstream of the kidneys. For the portal vein injections, the portal vein and hepatic artery were clamped. The outflow through the hepatic vein was restricted in some animals by clamping the upstream and downstream IVC. In some animals the livers were first flushed with normal saline prior to DNA injection. Rat bile duct injections were done the same as mice. The rat doesn't have a gallbladder.

In some of the rat portal vein injections, a 25 G needle connected to a pressure gauge (Gilson Medical Electronics, Model ICT-1 1 Unigraph), was inserted into the liver parenchyma to determine the peak pressure within the liver during the injections. The statistical relationship between pressure and luciferase was done using Spearman's rank correlation. A smoothing spline regression model describing the relationship between log luciferase and pressure was estimated using generalized additive model methodology (Hastie, 1992). Akaike's information criteria (Akaike,. 1973) indicated that a smoothing spline with 2 degrees of freedom resulted in the best fit over all integer degrees of freedom between 0 and 5.

The injections in dogs were done as in rats except that an 18 gauge, 2 inch angiocath (Becton Dickinson, San Jose, Calif.) was used. All dogs except dog #1 were females. Table I indicates the injection conditions. For the bile duct injections, a suture was applied to occlude transiently the bile duct downstream from the point of injection. A DeBakey multipurpose vascular clamp was applied to the cystic duct during injection to prevent the injectate from entering the gallbladder. In dogs, the DNA was pCILux.

Protein Assays: The luciferase assays were done as previously reported (Wolff, et al., 1990). One day after pCILuc injections, the animals were sacrificed and the rodent livers were divided into 6 sections composed of right lateral lobe, caudate lobe, two pieces of median lobe and two pieces of left lateral lobe. For each of the six pieces, 0.7 ml of lysis buffer (0.1% Triton X-100, O.1 M potassium phosphate, 1 mM DTF pH 7.8) was used for mice and four ml of lysis buffer were used for rat liver. For the dog livers, approximately 10% of each lobe was divided into five to 20 pieces and placed into two ml of lysis buffer. The samples were homogenized using a PRO 200 homogenizer (PRO Scientific Inc., Monroe, Conn.) and centrifuged at 4,000 rpm for 10 min. at 4EC. Twenty:1 of the supernatant was analyzed for luciferase activity. Relative light units (RLU) were converted to pg of luciferase using standards from Analytic Luminescence Laboratories (ALL, San Diego, Calif.). Luciferase protein (pg)=$5.1 \times 10^{-5} \times RLU + 3.683$ ($r^2$=0.992).

Ten-μm thick tissue sections were stained for Ǝ-galactosidase expression as previously described using 1–4 hour X-GAL incubations (Budker, et al., 1996). Hematoxylin was used for the counterstain but the alkaline step was omitted so that the hematoxylin stain remained red. The percent of blue-stained cells in the liver sections was determined by counting ~3000 cells in three sections and averaging.

Blood obtained from the retro-orbit sinus was analyzed for serum concentration of hGH using the RIA, HGH-TGES 100T kit from Nichols Institute (San Juan Capistrano, Calif.). Serum ALT and GGT levels were done using EKTACHEM DT slides and a KODAK EKTACHEM DT 60 ANALYZER as recommended by the manufacturer (Kodak, Rochester, N.Y.).

Mice Luciferase Experiments: Our previous studies used the pBS.CMVLux plasmid for evaluating the optimal conditions for naked pDNA expression following importal injection. These optimal conditions were intraportal injections of 100:g of pDNA in 1 ml of 15% mannitol and 2.5 units heparin/ml in normal saline solution. The injections were done over 30 seconds with the hepatic vein and IVC occluded. In this study, 100:g of pCILuc injected under similar conditions yielded a mean total luciferase protein/liver of 3.73:g/liver, approximately 30- times greater than that obtained with pBS.CMVLux. Part of this increase could be attributed to greater operator experience with these injection techniques. Injections with pCILuc under these conditions without clamping the hepatic vein yielded approximately 750-fold less luciferase.

The hepatic veins (via the IVC) of another set of mice were injected with 100:g of pCILuc in 1 ml of 15% mannitol and 2.5 units heparin/ml in normal saline solution. A mean total luciferase protein/liver of 17.34:g/liver was obtained when the portal vein was clamped as compared to a mean total luciferase protein/liver of 2.83:g/liver without occluding the portal vein.

Similar results were also obtained when bile ducts were injected with 100:g of pCILuc in 1 ml of 15% mannitol and 2.5 units heparin/ml in normal saline solution. A mean total luciferase protein/liver of 15.39:g/liver was obtained when the hepatic vein was clamped as compared to a mean total luciferase protein/liver of 1.33:g/liver without occluding the hepatic vein. If mannitol was omitted then the bile duct injections without clamping any blood vessels yielded approximately 15-fold less luciferase (0.086:g/liver ±0.06, n=25). Clamping the hepatic artery, and portal vein in addition to the hepatic vein did not improve expression beyond what was obtained when only the hepatic vein was clamped (data not shown).

Serum ALT and GGT assays were performed on mice one and eight days after each of the above injections with pCILuc (4 mice for each condition). No increases in GOT were observed after any of the injections including the bile duct injections. Serum ALT levels increased to 200–400 U/L one day after portal vein and bile duct injections. One day after IVC injections serum ALT levels increased to ~1500 U/L in half of the mice but was only ~250 U/L in the other half. By eight days after injection, serum ALT levels decreased to baseline levels in all animals. For positive control purposes, a non-lethal intraperitoneal injection of 40:1 of 50%, carbon tetrachloride in mineral oil was performed. An average of 25,900 U/L (n=4) was observed one day after injection.

Rat and Dog Luciferase Experiments: Similar injections into the portal vein, IVC (to the hepatic vein), and bile duct were done in rats. For the portal vein injections, the injection volumes were increased 15-times over that used in mice because the rat livers are ~15-times larger than mouse livers. One day after 750:g of pCILuc in 15 ml of 15% mannitol and 2.5 units heparin/ml in normal saline solution were injected into the portal vein while occluding the hepatic vein, an average of 53.5:g of luciferase/liver was obtained. The efficiency of gene transfer in the rat was compared to that in mice two ways. In terms of efficiency as defined by the mg of luciferase per mg of tissue weight, the levels of expression for portal injections were 3.6:g of luciferase/g of tissue in rats as compared to 3.7:g of luciferase/g of tissue in mice. Alternatively, in terms of efficiency as defined by the ng of luciferase per:g of pDNA delivered, the efficiencies of expression for portal injections were 71 ng of luciferase/:g DNA in rats as compared to 37 ng of luciferase/:g DNA in mice.

Less but still substantial luciferase expression was obtained when the injections of pCILuc were done into the efferent vessels of rats such as the IVC or bile duct. Injections of 750:g of pCILuc in 15 ml into the hepatic vein (via the IVC) while occluding the portal vein yielded an average of 1.5:g of luciferase/liver. Injections of 750:g of pCILuc in 5 to 8 ml into the bile duct without any outflow obstruction yielded an average of 1.3:g of luciferase/liver.

Parenchymal pressures of 12–50 mm Hg were measured in 23 rat livers during the injection of 750:g pCILuc in 15 or 20 ml into the portal vein while occluding the IVC. Spearman's rank correlation between pressure and luciferase expression was 0.76 (two-side p-value <0.001) indicating that pressure and luciferase were significantly positively associated. It appeared that pressures of over 40 mm Hg did not result in increased expression. The necessity of the non-linear component over and above a simple linear fit was verified by an approximate full versus reduced F-test (p-value=0.0 14), indicating that the observed plateau effect is real. Examination of both the residual quantile-quantile and the residual versus prediction plots further reveals that there are no serious violations of the regression model assumptions and therefore the regression models and p-values are valid (Fisher and van Belle, 1993).

Preliminary experiments explored the ability of naked pCILux (not pCILuc) to be expressed in dogs (Table I). In mice, in the case of intraportal injection, pCILux provided 3× lower expression than pCILuc (data not shown). In five dogs, various amounts of DNA were injected into either the bile duct with or without blocking outflow by occluding the IVC. In one animal, the DNA was injected into the IVC without any outflow blockage. All the dogs survived the procedure except animals that had the IVC occluded recovered more slowly post-operatively. The animals were sacrificed one day after the injections and dozens of tissue samples from each liver lobe were analyzed for luciferase. The luciferase expression was evenly distributed over all the lobes in each liver except in one lobe of one dog. Routine histological analysis in dog #5 (Table I) indicated that the tissue architecture was substantially disrupted suggesting that the injection volumes were too large.

Decreasing the volume of injection in dog #6 to 200 ml resulted in the best expression (Table I).

Mice and Rat β-Galactosidase Results: The Ǝ-galactosidase expression vector was used to determine the percent and type of cells that were transfected. As previously noted for portal vein injections (Budker, et al., 1996), the vast majority of the blue-stained cells appeared to be hepatocytes on morphological grounds but a few appeared to be endothelial or other types of cells. A preponderance of hepatocytes were also stained blue after the bile duct or IVC injections in mice or rats.

Under the various injection conditions, the percent of cells paralleled the levels of luciferase expression. In mice, the IVC injections gave the highest percentage of β-galactosidase-positive cells in which 7% of hepatocytes were positive. In rats, the portal vein injections gave the highest percentage of β-galactosidase-positive cells in which 7% of hepatocytes were positive. In some animals, liver cell damage was evident in less than 5% of the cells. Of note in the rat livers injected into the portal vein, almost all of the positively-stained cells were periacinar with few positive cells around the central vein.

Repeat Bile Duct Injections: The bile ducts of mice were cannulated and 100:g of pCMVhGH in 1 ml of 15% mannitol in normal saline were injected once a week. Serum levels of hGH increased one day after the fast injection and then decreased to background levels by seven days after injection. One day after the second injection, hGH levels again increased and then were back to background levels by seven days after the second injection. Only minimal increases in hGH levels occurred after the third injection. Mice that had the highest levels after the first injection had the lowest levels after the second injection (mice 3 and 6) and vice versa (mice 1, 2, and 4). In another set of animals (4 mice), the bile duct injections were repeated four times with pCMVhGH and then pCILuc was injected. The first three pCMVhGH injections led to similar increases in hGH serum levels. Although there were only minimal raises in hGH serum levels following the fourth injection, injection of pCILuc yielded an average of 29.2 ng/liver (±7.1, n=3). The liver in one of the four mice was grossly yellow and scarred as a result of the bile duct ligation and did not express any luciferase.

Discussion

This report extends the findings of the previous study showing pDNA expression following afferent intraportal delivery and demonstrates efficient plasmid expression following delivery via efferent vessels such as the hepatic vein or bile duct. Expression of luciferase or β-galactosidase was evenly distributed throughout the entire liver when either of the three vessels were injected. Combining these surgical approaches with improved plasmid vectors enabled uncommonly high levels of foreign gene expression in which over 15:g of luciferase protein/liver was produced in mice and over 50:g in rats. Equally high levels of β-galactosidase expression were obtained in that 7% of the hepatocytes had intense blue staining with only a one hour X-GAL incubation. These levels of foreign gene expression are among the highest levels obtained with nonvital vectors and approach what can be achieved with vital vectors.

Using the portal vein administration route, occlusion of the outflow is critical for expression. Outflow occlusion increases the expression with the efferent administrative routes, but substantial amounts of expression were obtained even when the hepatic vein was not blocked. Most likely the natural direction of blood flow provides a sufficient impetus to retard the egress of injection fluid and raise the hydrostatic pressure. The use of these efferent vessels simplifies the administration for potential human applications since they are easier to access by non-invasive methods. If no occlusion is used then only one vessel has to be reached. These efferent routes should also be considered for the administration of viral and non-viral vectors as has been done with the delivery of adenoviral vectors into the bile duct [Vrancken Peeters, et al., 1996b; Vrancken Peeters, et al., 1996a; Yang et al., 1993).

The mechanism of pDNA uptake is not known but may involve native cellular uptake processes (Budker, et al., 1996). It is of interest that high levels of luciferase expression could occasionally be obtained when the DNA was injected into the bile duct in small volumes of isotonic solutions without occluding the IVC. Increased osmolar and hydrostatic pressure may not be critical for uptake of the pDNA by hepatocytes as they are not in muscle cells (Wolff, et al., 1990; Wolff, et al., 1991; Wolff, et al., 1992a). This would suggest that the mechanism of pDNA uptake may in fact involve endogenous cellular pathways. Increased hydrostatic and osmotic pressures may raise expression by enhancing these cellular internalization processes (Haussinger, 1996). For example, hepatocyte shrinkage stimulates replication of the duck hepatitis B virus (Offensperger, et al., 1994).

The raised pressures could also increase the delivery of the pDNA to the hepatocyte surface not only for the blood vessel administrations (through the sinusoidal fenestrae) but for the bile duct injections as well. The increased pressures could transiently attenuate bile secretion thereby decreasing the clearance of the pDNA (Stieger, et al., 1994). For example, the hyperosmolar mannitol should induce cell shrinkage that is known to inhibit taurocholate excretion into bile (Haussinger, et al., 1992).

Hepatocytes are functionally polarized cells in which the basal and apical membranes have different exocytic, endocytic and transcytotic functions (Hubbard, et al., 1994). The success with either blood vessel or bile duct routes could indicate that both the basal (sinusoidal) and apical (bile canalicular) membranes share a common pathway for the cellular entry of pDNA. However, the passage of DNA between the basal-lateral and bile canalicular spaces cannot be excluded even under the more gentle injection conditions. Plasmid DNA injected into the bile duct could be taken up from the basal-lateral surface of hepatocytes after passage pancellularly. If only the basal-lateral surface takes up the pDNA then the increased hydrostatic and osmotic pressures may enhance pDNA expression by disrupting the tight junctions between hepatocytes and thereby increase the flow of pDNA between the canalicular and basal-lateral spaces (Desmet and De Vos, 1982).

The bile duct was cannulated to determine whether repeat injections could be done. Substantial hGH levels were obtained alter the first two injections. The hGH levels dropped considerably by one week after each injection presumably because of an immune response to the foreign protein. The inability to detect hGH after the third or fourth injections was most likely due to a more rapid response of the immune response sensitized to hGH. The ability to subsequently obtain luciferase expression argues against an immune response against the pDNA that prevents expression. Previous studies have failed to detect anti-DNA antibodies following the administration of naked pDNA (Nabel, et al., 1992; Jiao, et al., 1992). The ability to repetitively administer naked pDNA without inducing an immune response against the vector is a distinct advantage of naked pDNA over viral and some other types of non-viral vectors.

Other studies in progress in our laboratory suggest that suppression of the immune system enables more persistent expression. In post-mitotic myofibers, plasmids can persist extrachromosomally and express for at least two years; presumably because the pDNA is not being lost as result of cell division (Wolff, et al., 1992b; Herweijer, et al., 1995). Quite possibly pDNA would be lost slowly in hepatocytes which have a half-life of up to a year in rodents and humans (Webber, et al., 1994; Leffert, et al., 1988). If so then liver-based genetic disorders such as hemophilia could be treated by injections every six months. The bile duct could be accessed repeatedly by upper gastrointestinal endoscopy. Similarly, the hepatic vein could be non-invasively accessed via peripheral or central veins. In addition, gene transfer could be delivered to newborns via the umbilical cord vessels to get them over a newborn metabolic crisis as occurs in the organic acidunas and the urea cycle defects.

Often gene transfer techniques that work in mice do not work in larger animals. Our results demonstrate that the technique works in rats that are approximately ten-fold bigger than mice. The dog results indicate that the liver of larger non-rodent mammal can express naked pDNA. Although substantial levels of luciferase activity were obtained, further optimization of the injection conclidons is required to increase the efficiency of expression so that they are comparable to those in rodents. The studies to determine the relationship between intraparenchymal pressure and luciferase expression in rats are a first step towards this goal. Minimal liver cell damage occurred in the rodents as evident by serum chemistries and histology but the injections were more disruptive to the hepatocytes in dogs. Presumably, the key factor is the efficient delivery of the pDNA to the hepatocyte surface with minimal cellular or tissue disruption.

In the research laboratory, the described techniques will enable rodents to be used just as immortalized and primary liver cell cultures are now used for gene and cellular studies of liver function. The transfer of genes into cells in culture have been a critically important tool for deciphering the function of genes and for studying the effect of expressed proteins on cellular processes. Typically, the gene under study is placed within a plasmid vector and transiently transfected into the appropriate cell in culture. Isoforms and mutant forms of the gene under study can be quickly placed into plasmid expression vectors and studied. Our findings indicate that a similar plasmid-based approach could be used to study the effects of gene function in hepatocytes in situ. Given that the high levels of expression are transient in this system, it would be best if these effects occurred within a few days. The use of pDNA avoids the laborious steps necessary for the production of vital vectors or generation of transgenic mice and thereby enables many different genes and their related mutated forms to be quickly studied. It will permit are mechanism of gene expression and their effects on liver function to be expeditiously probed within the context of a complete mammalian organism.

Example 12

The intravascular delivery of naked pDNA to muscle cells also has attraction. Muscle has a high density of capillaries (Browning, 1996) and the capillaries are in close contact with the myofibers (Lee 1995). However, the endothelium in muscle capillaries is of the continuous, non-fenestrated type and has low solute permeability especially to large macromolecules (Taylor, A. E., and D. N. Granger. Exchange of macromolecules across the microcirculation. In: Handbook of Physiology. The Cardiovascular System. Microcirculation. Bethesda, Md.: Am. Physiol. Soc., 1984, sect. 2, vol. IV, chapt. 11, p. 467) The mechanism of macromolecule transendothelial transport is poorly understood. Cell biologists have proposed that this transport occurs by transcytosis involving plasmalemmal vesicles or convective transport through transient transendothelial channels formed by the fusion of vesicles. (Michel C. C. Cardiovascular Res. 1996). Physiologists have modeled the muscle endothelium as having a large number of small pore with radii of 4 nm and a very low number of large pores with radii of 20–30 nm. (Rippe B. Physiological Rev, 1994). Although the radius of gyration of 6 kb pDNA is ~100 nm (Fishman, D. M., Biopolymers, 38, 535–552), supercoiled DNA in plectonomic form has superhelix dimensions of approximately 10 nm (Rybenkov V. V. J. Mol. Biol. 267, 299–311 1997). This implies that pDNA has a possibility to traverse microvascular walls by stringing through their large pores. We hypothesized that the rate of pDNA extravasation could be increased by enhancing fluid convection through these large pores by raising the transmural pressure difference in selective regions. This report demonstrates that intravascular pDNA injections under increased pressure can in fact lead to high levels of foreign gene expression in muscles throughout the selected hindlimb of an adult rat.

Hydrostatic Pressure 475 ug of pCILux in normal saline solution (NSS) was injected into the femoral arteries of adult Sprague-Dawley rats while blood inflow and outflow were blocked. Injection of pCILux, a luciferase expression vector utilizing the CMV promoter (LIVER II promoter accepted for HGT), was done after both the femoral artery and vein was occluded for 10 min. Two days after pDNA injections, the luciferase activities were measured in all the muscles of the hindlimb. The highest levels of luciferase expression were achieved when the pCILux was injected in 9.5 ml of normal saline within 10 sec. Injection volumes less than 9.5 ml resulted in substantially less expression. Injection times more than 10 sec also resulted in much less expression. This critical dependence on volume and speed of injection indicates that either increased hydrostatic pressure or rapid flow is required for efficient expression. Artery injections performed without occluding the femoral vein resulted in approximately 200-fold less expression (1.8±1.2 ng of luciferase per all hindlimb muscles).

Other Factors

Further studies were performed to determine the effect of ischemia on the expression of the intravascularly injected pCILux. The time of ischemia was adjusted by varying the time that both the femoral artery and vein were occluded prior to pDNA injection. Although the highest level of expression was obtained with 10 min of ischemia, the expression levels were only a few-fold lower at shorter or longer ischemia times. This suggests that ischemia is not a critical factor for enabling egress of the pDNA out of the intravascular space. However, the blood flow for the zero ischemia time point is disrupted for ~30 sec and this may be sufficient to affect vascular permeability. Ischemia could increase expression either by capillary recruitment and vasodilatation) or augmenting permeability (Mathieu-Costello O. Int J Microcirc 1995, 15, 231–237). In addition, ischemia could possibly increase pDNA expression by affecting transcription or translation. Ischemia can be tolerated by muscle for two to three hours (Gidlof A., Int. J. Microcirc. Clin. Exp. 1987, 7,67–86). Histologic analysis of the muscle did not reveal any hemorrhage or myofiber damage.

Other factors were explored to increase the level of expression. Hypotonic or hypertonic injection solutions resulted in less expression. Although, the effect of the hypertonic injection solution (normal saline solution with 15% mannitol) may have been mitigated by the slower rate of injection (over 30 sec instead of 10 sec) that results from its increased viscosity. The pre-injection with collagenase resulted in a 3.5-fold increase to 1,332 ng/total muscles. The collagenase was used to disrupt the basement membrane of the capillaries and thereby increase pDNA egress. It could have also increased expression by disrupting the extracellular matrix within the muscle. Further studies are in progress to determine the optimal conditions for collagenase administration without causing hemorrhage.

Distribution of Foreign Gene Expression

The luciferase expression was distributed among all muscle groups in the leg (Table 1). The lower levels in the lower anterior leg and foot are probably due to their high content of tendons and small amount of muscles. The levels after intravascular injection was up to 40 times higher than the levels after intramuscular injection.

The type and percentage of the transfected cells in the muscle were determined using the β-galactosidase reporter system. Using the best injection condition, approximately 10–50% of the myofibers expressed β-galactosidase.

These expression results provide indirect evidence that pDNA extravasation occurred. More direct evidence was obtained using fluorescently-labeled DNA injected into the femoral artery. The labeled DNA was distributed extravascularly in all the limb muscles and surrounded most of the myofibers (data not shown).

Conclusion

These results demonstrate that the intraarterial delivery of pDNA to muscle can be greatly enhanced when injected rapidly, in a large volume and when all blood vessels leading into and out of the hindlimb are occluded. These conditions presumably increase the intravascular hydrostatic pressure and thereby increase the convective outflow that transports the pDNA into contact with myofibers. The increased intravascular pressure may increase the number, size and permeability of the microvascular pores (Rippe, B. Acta Physiol. Scand. 125, 453–459, 1985) (Wolf, M. B. Am. J. Physiol. 257, H2025–H2032,1989). Preliminary studies using collagenase suggest that enzymatic disruption of the vessels basement membrane or muscle extracellular matrix may also increase the delivery of pDNA to the myofibers. Ischemia also increased expression moderately. Furthermore, it is expected that other enzymes such as hylaronidase will perform similarly to collagenase.

This study shows that the intravascular approach increases expression in muscle up to 40-fold as compared to intramuscular injection. This is the first demonstration that naked plasmid DNA can be efficiently expressed in muscles of adult animals larger than mice. It is also the first report of an intravascular non-viral gene transfer approach for muscle. Further studies in larger animals will determine the clinical relevance of this study.

Description of Injections

A 4 cm long abdominal midline excision was performed in 150–200 g, adult Sprague-Dawley rats anesthetized with 80 mg/mg ketamine and 40 mg/kg xylazine. Microvessel clips (Edward Weck, Inc., Research Triangle Park, N.C.) were placed on external iliac, caudal epigastric, internal iliac and deferent duct arteries and veins to block both outflow and inflow of the blood to the leg. A 27 g butterfly needle was inserted into the external iliac artery and the DNA solution was injected by hand.

TABLE 1

Distribution of luciferase expression among the different hindlimb muscle groups two days following intraarterial injection with 475 μg of pCILux in 9.5 ml of NSS over 10. Means and their standard deviations are shown for 6 animals.

| Injection type | Muscle group | Total Luciferase (ng) | Luciferase Conc. (ng/g tissue) |
|---|---|---|---|
| Intravascular | Upper Leg Anterior | 149.1 ± 51.2 | 109.2 ± 37.5 |
| | Upper Leg Posterior | 74.6 ± 36.0 | 43.4 ± 20.9 |
| | Upper Leg Medial | 88.7 ± 63.7 | 61.6 ± 44.5 |
| | Lower Leg Posterior | 114.5 ± 89.7 | 66.0 ± 51.7 |
| | Lower Leg Anterior | 3.0 ± 1.0 | 5.4 ± 1.7 |
| | Foot | 0.5 ± 0.2 | 4.1 ± 1.4 |
| Intramuscular | Upper Leg Anterior | 3.7 ± 0.9 | 2.8 ± 0.8 |

Example 13

Adenoviral vectors can be delivered to muscle parenchymal cells by an intravascular route.

Methods: the same methods that were used to deliver naked plasmid DNA to muscle in rats were also used. The adenoviral vector CMVLacZ that expresses the *E. coli* beta-galactosidase from the immediate early promoter of the human cytomegalovirus (commonly called the "CMV promoter") was prepared as previously described (Yang, T., K. U. Jooss, Q. Su, H. C. J. Ertl and J. M. Wilson: *Immune responses to viral antigens versus transgene product in the elimination of recombinant adenovirus-infected hepatocytes in vivo*, Gene Therapy, 3(2): 137–144, 1996) The rat iliac artery was preinjected with 0.5 mg of papaverine and 40 ng of collagenase in 3 ml of saline while blocking the iliac artery and vein. $5 \times 10^8$ particles of the adenoviral vector CMVLacZ in 10 ml of saline was injected in about 10 sec and 2 minutes later the clamps were opened. Two days after injection the leg muscle were assayed for luciferase as above.

Results:

TABLE

Distribution of luciferase activity following the intraarterial injection of adenovirus CMVLacZ.

| Muscle Group | Luciferase (ng) |
|---|---|
| Upper Leg Anterior | 59.04 |
| Upper Leg Posterior | 18.33 |
| Upper Leg Medial | 4.44 |
| Lower Leg Posterior | 11.04 |
| Lower Leg Anterior | 5.33 |
| Foot | 0.22 |
| Total | 98.40 |

Example 14

Surgical Description—Cynomolgus monkeys (n=6) weighing 2.5 to 3.3 kg and were sedated with ketamine (10–15 mg/kg IM). After sedation, animals were intubated and anesthesia was maintained with 1.0 to 2.0% isoflurane. An intravenous catheter was inserted into the cephalic vein for administering fluids and EKG electrodes were attached to the limbs for monitoring heart rate. The surgical area was prepped and draped for surgery using aseptic technique. A femoral cutdown was performed and a 5 cm segment of the femoral vein was dissected free of connective tissue. The vein was ligated distally and a 6F introducer was inserted into the vein and secured with a vessel tourniquet. A 4F injection catheter was inserted through the introducer and advanced into the inferior vena cava (IVC). An abdominal incision was made extending from just below the xyphoid to the pubis. A retractor was placed inside the abdominal cavity and moist sponges were used to retract and hold the intestines. The infra hepatic IVC was exposed and the exact placement of the injection catheter within the IVC was adjusted so that the tip of the catheter was adjacent to the hepatic vein. A vessel tourniquet was placed loosely around the infra hepatic IVC to prevent backflow during the nucleic acid injection. The supra hepatic IVC was dissected free of connective tissue and ligament attachments. In some animals (n=3), a catheter (20 gauge) was inserted into the portal vein and attached to a pressure transducer to measure pressure changes during the injection. Immediately before the injection, a vascular clamp was placed on supra hepatic IVC and the vessel tourniquet was tightened around the infra hepatic IVC. The IVC remained occluded during the injection and for 2 minutes post injection. After the injection, the clamps were removed and the portal vein pressure catheter was pulled. The abdominal cavity was closed in 3 layers with 3–0 PDS suture. The catheter and introducer were pulled from the femoral vein, the vessel was ligated and the incision was closed in 2 layers with 3–0 PDS suture. Prior to the completion of the surgery, the animal was given buprenorphine (0.005–0.01 mg/kg IM) as an analgesic. Blood samples were collected on days 0, 1, 4, 7, 14 and 21 for measuring reporter gene expression (secreted alkaline phosphatase), liver enzymes and a complete blood count.

Injection description—Two 60 ml syringes were filled with a total volume of 120 ml of injection solution containing 0.9% NaCl, 7.5% mannitol and 10 mg of CMV-SEAP. Syringes were attached to a syringe pump (Harvard Instrument) and connected to the injection catheter via an extension line with a 3-way stopcock. The injection flow rate was set at either 60, 120 or 160 ml/min. In addition to using the syringe pump, hand injections were performed on two animals. The flow rate was continuous during the injection except for one animal that had a preset pause (5 seconds) half way through the injection. During the injection, the entire liver swelled and patchy areas were blanched from the injection solution. In five of the six animals, it was noted that the liver swelled to the point where fluid would begin to leak out the exterior of the liver capsule by the end of the injection.

Pressure—The portal vein pressure during injection was measured at two injection flow rates. An injection rate of 120 ml/min produced a transient elevation in portal vein pressure to 45 mm Hg while a flow rate of 160 ml/min resulted in a pressure increase to 105 mm Hg. This pressure increase lasted for the length of the injection and rapidly returned to preinjection levels.

Toxicity—All animals recovered and regained normal activity within 24 hours after surgery.

Liver enzymes were elevated in all animals after surgery with the highest levels on day 1. Enzyme levels gradually declined thereafter and returned to normal levels around day 14. Day one levels of alanine aminotransferase (ALT) varied from 4960–338 U/L. The animals with the highest ALT levels were also the animals with the highest level of gene expression. One of the animals that showed both high reporter gene expression and elevated liver enzymes was sacrifice at 21 days to harvest tissue for histology. H+E slides of the right and left lobes showed normal tissue with no significant pathology.

Reporter Gene Expression—In all the animals in this study, reporter gene expression peaked at day 2. The first animal (animal #1) in this study was a hand injection and resulted in the highest gene expression (day 2=2414 ng/ml SEAP) in this study. This hand injection delivered ~120 ml of solution/minute. Using a syringe pump we found that 60 ml/min (animal #3) and 120 ml/min (animal #2) resulted in a low level of gene expression on day 2 (99 and 71 ng/ml SEAP respectively) but a flow rate of 160 ml/min (animal #5) dramatically improved expression (day 2=1991 ng/ml SEAP). This injection rate was repeated in a second animal (animal #6) but with a preset pause (5 seconds) halfway through the injection to determine if continuous flow was important for high gene expression. The expression in this animal was also high (day 2=985 ng/ml) but lower than the continuous syringe pump injection. In one additional animal, the pump failed during the injection and had to be helped by hand (animal #4). This injection delivered 120 ml in approximately one minute and resulted in a SEAP level of 350 ng/ml on day 2.

TABLE

Hepatic Vein Delivery of Nucleic Acid to Primate Liver. Expression of plasmid CMV-SEAP in liver and analysis of toxicity.

| animal | day | | | | | | |
|---|---|---|---|---|---|---|---|
| | 0 | 1 | 2 | 4 | 7 | 14 | 21 |
| | SEAP expression (ng/ml) | | | | | | |
| 1 | | 2300.7 | 2414.7 | 1605.1 | 1144.1 | 504.2 | 0.7 |
| 2 | | 70.9 | 70.8 | 43.4 | 18.0 | 3.4 | 1.6 |
| 3 | | 63.9 | 98.8 | 85.5 | 49.5 | 13.4 | 9.2 |
| 4 | | 206.7 | 350.1 | 184.9 | 59.3 | 55.7 | 2.5 |
| 5 | | 1686.1 | 1990.7 | 1737.8 | 831.9 | 371.7 | 155.8 |
| 6 | | 740.9 | 985.1 | 864.4 | 634.6 | 232.5 | 106.7 |
| | ALT | | | | | | |
| 1 | | 3148 | 1758 | 669 | 239 | 92 | 71 |
| 2 | 22 | 338 | 198 | 90 | 45 | 39 | 21 |
| 3 | 25 | 885 | 468 | 209 | 95 | 44 | 28 |
| 4 | 39 | 725 | 499 | 224 | 112 | 57 | 40 |
| 5 | 51 | | | 438 | 207 | 57 | 41 |
| 6 | 54 | 4960 | | 2116 | 767 | 148 | 70 |
| | white blood cell count | | | | | | |
| 1 | 4.1 | 4.5 | | | 8.5 | 6.3 | 5.5 |
| 2 | 15.8 | 13.1 | 17.9 | 16.6 | 14.0 | 17.0 | 14.0 |
| 3 | 15.4 | 10.2 | 9.6 | 11.6 | 12.4 | 15.5 | 10.3 |
| 4 | 6.7 | 11.8 | 8.9 | 11.6 | 10.4 | 9.7 | 8.9 |
| 5 | 8.1 | 12.8 | 8.1 | 10.2 | 8.2 | 15.3 | 13.0 |
| 6 | 8.5 | 17.6 | | 12.0 | 8.4 | 8.6 | 7.9 |
| | ALKP | | | | | | |
| 1 | | 1122 | 1353 | 896 | 566 | 219 | 148 |
| 2 | 164 | 287 | 288 | 218 | 188 | 237 | 210 |
| 3 | 182 | 301 | 372 | 272 | 249 | 223 | 196 |
| 4 | 134 | 250 | 303 | 235 | 195 | 161 | 140 |
| 5 | 165 | 1147 | 1407 | 1036 | 831 | 443 | 295 |
| 6 | 251 | 560 | | 931 | 632 | 392 | 322 |
| | CPK | | | | | | |
| 1 | | 2987 | 918 | 380 | 208 | 131 | 233 |
| 2 | 361 | 1180 | 246 | 164 | 138 | | 235 |
| 3 | 1253 | 3769 | 1250 | 188 | 210 | 91 | 318 |
| 4 | 411 | 1358 | 554 | 227 | 107 | 99 | 184 |
| 5 | 487 | 1600 | | 787 | 421 | 112 | 680 |
| 6 | 789 | 12800 | | 451 | 382 | 2027 | 333 |
| | AST | | | | | | |

TABLE-continued

Hepatic Vein Delivery of Nucleic Acid to Primate Liver. Expression of plasmid CMV-SEAP in liver and analysis of toxicity.

| animal | day | | | | | | |
| --- | --- | --- | --- | --- | --- | --- | --- |
| | 0 | 1 | 2 | 4 | 7 | 14 | 21 |
| 1 | | 973 | 169 | 47 | 36 | 37 | 39 |
| 2 | 29 | 102 | 48 | 26 | 32 | 40 | 31 |
| 3 | 29 | 360 | 101 | 27 | 33 | 28 | 20 |
| 4 | 26 | 156 | 69 | 38 | 36 | 26 | 24 |
| 5 | 32 | 515 | 122 | 47 | 50 | 36 | 43 |
| 6 | 32 | 6617 | | 90 | 50 | 56 | 31 |
| GGT | | | | | | | |
| 2 | 59 | 71 | 65 | 56 | 57 | | 60 |
| 3 | 83 | 105 | 97 | 80 | 85 | 84 | 78 |
| 4 | | 76 | 73 | 69 | 72 | 73 | 74 |
| 5 | 42 | 88 | 78 | 68 | 72 | 57 | 57 |
| 6 | 137 | 119 | | 154 | 146 | 153 | 158 |

The foregoing is considered as illustrative only of the principles of the invention. Further, since numerous modifications and changes will readily occur to those skilled in the art, it is not desired to limit the invention to the exact construction and operation shown and described.

We claim:

1. A process for delivering a polynucleotide to a primate liver cell, comprising:
   a) transiently occluding afferent and efferent blood vessels of the liver in a primate; and,
   b) injecting the polynucleotide in a solution into the lumen of a hepatic vessel wherein the injection of the solution results in portal vein pressure of 10 mm Hg or greater.

2. The process of claim 1 wherein the solution is injected at a rate of 18 ml/kg/min or greater.

3. The process of claim 1 wherein the solution is injected at a rate of 36 ml/kg/min or greater.

4. The process of claim 1 wherein the solution is injected at a rate of 48 ml/kg/min or greater.

5. The process of claim 1 wherein the injection of the solution results in portal vein pressure of 45 mm Hg or greater.

6. The process of claim 1 wherein the injection of the solution results in portal vein pressure of 105 mm Hg or greater.

7. The process of claim 1 wherein the polynucleotide consists of naked DNA.

8. The process of claim 1 wherein the polynucleotide is selected from the group consisting of a viral vector and a non-viral vector.

9. The process of claim 1 wherein the polynucleotide consists of a blocking polynucleotide for preventing gene expression.

10. The process of claim 9 wherein the blocking polynucleotide consists of antisense.

11. The process of claim 9 wherein the blocking polynucleotide consists of siRNA.

12. The process of claim 1 wherein the hepatic vessel consists of a hepatic vein.

13. The process of claim 1 wherein the hepatic vessel consists of a hepatic artery.

14. The process of claim 1 wherein the hepatic vessel consists of a portal vein.

15. The process of claim 1 wherein the hepatic vessel consists of a bile duct.

* * * * *